US006800452B1

(12) United States Patent
McNeil et al.

(10) Patent No.: US 6,800,452 B1
(45) Date of Patent: *Oct. 5, 2004

(54) AUTOMATED METHODS FOR SIMULTANEOUSLY PERFORMING A PLURALITY OF SIGNAL-BASED ASSAYS

(75) Inventors: John Austin McNeil, La Mesa, CA (US); Michael Anthony Akong, San Diego, CA (US); Donald James Mierzeski, La Jolla, CA (US); Gonul Velicelebi, San Diego, CA (US); David Philip Karlton, San Diego, CA (US)

(73) Assignee: Science Applications International Corporation, San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 628 days.

(21) Appl. No.: 08/287,358

(22) Filed: Aug. 8, 1994

(51) Int. Cl.[7] ................................................. C12Q 1/02

(52) U.S. Cl. ....................................... 435/29; 435/288.7

(58) Field of Search ........................ 435/7.21, 29, 69.2, 435/287.1, 287.3, 288.4, 288.7, 968; 422/62, 63, 82.09

(56) References Cited

U.S. PATENT DOCUMENTS

| 3,604,927 A | | 9/1971 | Hirschfield | ............... 250/71 R |
| 4,343,782 A | * | 8/1982 | Shapiro | ......................... 424/3 |
| 4,443,104 A | * | 4/1984 | Ringhardtz | ................. 356/246 |
| 4,573,796 A | | 3/1986 | Martin et al. | ............... 356/318 |
| 4,626,684 A | * | 12/1986 | Landa | ........................ 250/328 |
| 4,626,693 A | | 12/1986 | Hirschfeld | |
| 4,713,781 A | | 12/1987 | Brizgis et al. | |
| 4,758,727 A | | 7/1988 | Tomei et al. | ............. 250/458.1 |
| 4,767,600 A | | 8/1988 | Vicario | ........................ 422/65 |
| 4,786,813 A | | 11/1988 | Svanberg et al. | ........ 250/461.1 |
| 4,816,395 A | | 3/1989 | Hancock et al. | |

(List continued on next page.)

FOREIGN PATENT DOCUMENTS

| EP | 0 441 755 A3 | | 8/1991 |
| WO | WO93/13423 | | 7/1993 |
| WO | WO 93/13423 | * | 7/1993 |

OTHER PUBLICATIONS

"Immunochemiluminometric Assay for Hepatitis B Surface Antigen," Hartmut R. Schroeder, et al., Clinical Chemistry, vol. 27, No. 8 (1981), pp. 1378–1384.

"Different Sensitivities to Agonist of Muscarinic Acetylocholine Receptor Subtypes," Hideaki Bujo, et al., FEBS Letters, vol. 240, No. 1,2; Nov. 21, 1988, pp. 95–100.

"Glutamate, the Dominant Excitatory Transmitter in Neuroendocrine Regulation," Anthony N. Van Den Pol, et al., Science, Nov. 30, 1990, pp. 1276–1278.

"Rapid Functional Assay for Multidrug Resistance in Human Tumon Cell Lines Using the Fluorescent Indicator Fluo–3", Dominic M. Wall, et al., Journal of the National Cancer Institute, vol. 83, No. 3, Feb. 6, 1991, pp. 206–207.

"Applications of Imaging Spectroscopy in Molecular Biology II. Colony Screening Based on Absorption Spectra," Adam P. Arkin, et al., Biotechnology, vol. 8, Aug. 1990, pp. 746–749.

"Fluorescence Assay in Biology and Medicine," Sidney Udenfriend, Molecular Biology, vol. II, published 1969, Academic Press, New York, pp. 176, 422–423, and 440–441.

"Special Techniques", Kinetics of Macromolecular Reations, published 1961, John Wiley & Sons, Inc., New York, pp. v (Preface), 656–57.

"Applications of Imaging Spectroscopy in Molecular Biology: I. Screening Photosynthetic Bacteria," Mary M. Yang, et al., Biotechnology, vol. 6, Aug. 1988, pp. 939–942.

"Quantitative Luminescence Imaging in the Biosciences Using the CCD Camera: Analysis of Macro and Micro Samples," Clair E. Hooper, et al., Trends in Analytical Chemistry, vol. 9, No. 8, 1990, pp. 269–277.

"Mobilization of Intracellural Calcium by $\alpha_1$–Andrenergic Receptor Activiation in Muscle Cell Monolayers", S. Kelly Amblert, et al., The Journal of Biological Chemistry, vol. 261, No. 13, pp 5866–5871.

Primary Examiner—Ralph Gitomer
(74) Attorney, Agent, or Firm—Banner & Witcoff, Ltd.

(57) ABSTRACT

An automated detection system includes a robotic fluid handling system for performing a plurality of assays; a detection system for imaging the assays as they are performed; and a computer control, data acquisition, and data analysis system for controlling the operation of the fluid-handling and detection system and for collecting and analyzing imaging data. The automated detection system comprises a pipettor for simultaneously distributing a predetermined amount of a liquid and a signal-generating element to each of the plurality of wells; an excitation source for simultaneously exposing the wells to excitation radiation; a detector for simultaneously detecting signal emitted from each of the wells over a period of time comprising a single imager for optically imaging the plurality of wells simultaneously; and computerized controller for simultaneously coordinating the pipettor, the excitation source, and the detector. Further, a method for performing simultaneous assays includes the steps of simultaneously distributing a predetermined amount of a liquid solution to each of a plurality of samples, simultaneously exposing the wells to excitation radiation, simultaneously detecting signals emitted from the wells using a detector comprising a single imaging means, and simultaneously controlling and coordinating the distribution, excitation, and detection using a computerized controller.

25 Claims, 18 Drawing Sheets

U.S. PATENT DOCUMENTS

| | | | |
|---|---|---|---|
| 4,826,660 A | 5/1989 | Smith et al. | 422/68 |
| 4,835,103 A | 5/1989 | Cercek et al. | 435/29 |
| 4,850,691 A | 7/1989 | Gardner et al. | |
| 4,877,965 A | 10/1989 | Dandliker et al. | 250/458.1 |
| 4,922,092 A * | 5/1990 | Rushbrooke et al. | 250/213 VT |
| 4,988,630 A | 1/1991 | Chen et al. | 436/533 |
| 4,992,092 A | 2/1991 | Birk et al. | 250/213 VT |
| 5,051,162 A | 9/1991 | Kambara et al. | 204/299 R |
| 5,053,626 A * | 10/1991 | Tillotson | 250/458.1 |
| 5,055,263 A | 10/1991 | Meltzer | 422/65 |
| 5,061,449 A | 10/1991 | Torti et al. | 422/100 |
| 5,073,029 A | 12/1991 | Eberly et al. | 356/432 |
| 5,082,628 A | 1/1992 | Andreotti et al. | |
| 5,087,820 A | 2/1992 | Kearns et al. | 250/385.1 |
| 5,091,652 A | 2/1992 | Mathies et al. | |
| 5,096,807 A | 3/1992 | Leaback | 435/6 |
| 5,097,135 A | 3/1992 | Makino et al. | |
| 5,104,621 A | 4/1992 | Pfost et al. | 422/67 |
| 5,112,134 A * | 5/1992 | Chow et al. | 356/427 |
| 5,115,137 A | 5/1992 | Anderson-Engels et al. | |
| 5,125,748 A * | 6/1992 | Bjornson et al. | 356/414 |
| 5,190,632 A | 3/1993 | Fujimiya et al. | 204/299 R |
| 5,202,091 A * | 4/1993 | Lisenbee | 422/52 |
| 5,208,685 A | 5/1993 | Aleksoff et al. | 359/19 |
| 5,262,128 A | 11/1993 | Leighton et al. | 422/100 |
| 5,355,215 A * | 10/1994 | Schroeder et al. | 356/317 |
| 5,407,820 A * | 4/1995 | Ellis et al. | 435/240.2 |

\* cited by examiner

ASP TEMPLATE 1

PIPETTE ASPIRATION PARAMETERS

- ACCEL(s/s/s): 300 / 1000 — 840, 841
- MAX SPEED (s/s): 437.2 / 1000 — 842, 843
- TIP START DEPTH (mm): 5.5 / 6 — 844, 845
- TIP DROP SPEED (s/s): 200 / 1000 — 846, 847
- TIME TO COMPLETE (ms): 10000 — 849

DISP TEMPLATE 1

PIPETTE DISPENSE PARAMETERS

- ACCEL(s/s/s): 300 / 1000 — 840, 841
- MAX SPEED (s/s): 300 / 1000 — 842, 843
- TIP START DEPTH (mm): 2.35 / 6 — 844, 845
- TIP RAISE SPEED (s/s): 200 / 1000 — 846, 847
- DROP BLOW OFF ☑ — 848
- TIME TO COMPLETE (ms): 10000

AUTOMATED METHODS FOR SIMULTANEOUSLY PERFORMING A PLURALITY OF SIGNAL-BASED ASSAYS

A portion of the disclosure of this patent document contains material which is subject to copyright protection. The copyright owner has no objection to the facsimile reproduction by anyone of the patent disclosure, as it appears in the Patent and Trademark Office patent files or records, but otherwise reserves all copyright rights whatsoever.

FIELD OF THE INVENTION

The present invention relates to an automated system for simultaneously performing a plurality of assays of test samples, detecting the results of the assays, and collecting and storing the data. The system comprises three major components: a detection system, a robotic fluid handling system, and a computer controlled data acquisition and data analysis system. The present invention further relates to a method for simultaneously performing a plurality of fluorescence assays, detecting the plurality of assays, and collecting, storing and analyzing the data.

BACKGROUND OF THE INVENTION

Signal-generating techniques are often employed to detect chemical reactions, biological events, and physical and chemical properties of a sample. Typically, the signal is in the form of radiation (e.g., light, color, fluorescence, luminescence, particle emissions) and either is a component/product of the reaction or is generated upon interaction of a component/product with an added indicator moiety.

An example of the use of signal generation to detect a biological substance is the quantitation of an antigen in biological samples using enzyme-linked immunosorbent assays (ELISA). In these assays, a sample is exposed to an enzyme-conjugated antibody capable of binding to the specific antigen to be detected. The conjugated enzyme is one that catalyzes a reaction which generates a signal (e.g., color, fluorescence, luminescence) that can be directly correlated with the amount of antigen in the sample. This type of assay, in which the property to be measured is constant and the signal is sustained, is referred to as an endpoint assay. Thus, in these assays, the signal is allowed to develop over time, and then a single signal measurement is taken after the reaction is complete in order to quantify the property.

In contrast to attributes that can be measured in endpoint assays, there are many properties, reactions and biological events that are dynamic and transient and/or rapidly occurring. For example, many cellular processes are rapid and transient in nature. Cells receive stimuli from the environment and must respond immediately for proper function and survival. Modulation of cell receptors and ion channels by binding of ligands can result in cellular responses such as changes in the levels of intracellular second messengers ($Ca^{2+}$, cyclic nucleotides, etc.). For instance, activation of a cell surface calcium channel upon binding of a ligand causes the channel to open and results in a rapid inward flux of calcium that transiently increases the intracellular $Ca^{2+}$ concentration which rapidly declines to preactivation concentrations. If the cell has been pre-loaded with a $Ca^{2+}$-sensitive fluorescent indicator, the change in intracellular $Ca^{2+}$ appears as a rapid increase and then decrease in fluorescence of the cell.

Because signal-generation techniques can provide information regarding the actual functioning of a cell, it is desirable to attempt to apply these methods to the identification of compounds that influence cellular activities (e.g., potential drugs that affect cell function through interaction with cell receptors, ion channels or enzymes). However, in drug screening procedures, large number of compounds are tested for cell modulation before even a small number are identified as potential drugs. The problems faced in using signal-generation techniques to detect and measure such transient and/or rapidly occurring phenomena in a single assay are only compounded in attempting to apply these techniques to the simultaneous performance of multiple assays for rapid screening of thousands of compounds.

For instance, the signal generated in these assays is rapidly occurring and transient, as is the phenomenon itself. Thus, in these assays, if initiation of the reaction or event (e.g., activation of the calcium channels by addition of ligand) is not coordinated with almost immediate signal detection in a dynamic fashion, the signal may reach a maximum and diminish before it is detected. In order to perform large-scale compound screening, coordination of sample handling and signal detection must be accomplished for many assays simultaneously. Furthermore, it is desirable to obtain a real-time record of each event until it has progressed to a point beyond that of maximum signal change. Thus, the duration, as well as the timing, of signal measurement poses an additional complication in these assays since the signal must be measured essentially constantly.

Accuracy of signal measurement is particularly critical in high-throughput screening assays of thousands of compounds. The need to perform a multitude of individual compound tests in a limited amount of time prohibits replicate assays of each compound. Additionally, sensitivity of signal detection presents another difficulty in signal-based assays of these phenomena. The signal changes accompanying these reactions or events are not only transient changes in the relative levels of the signal (i.e., increases in signal above a baseline level of signal), but may also be of relatively small magnitude. In large-scale drug screening, these transient, relatively small signal changes must be detected in multiple assays simultaneously.

Consequently, there is little margin for error in each single compound assay; an erroneous signal measurement by the detection system could result in elimination of a viable drug from further consideration. Additionally, signal measurement accuracy and sensitivity is essential in detecting small but significant differences in cellular responses to varying doses of compounds and in the response generated by an unknown compound as compared to a standard known drug.

Thus, there is a need for signal detection instrumentation that enables fully automated, high-volume assays of rapid, transient phenomena with sufficient sensitivity and the degree of accuracy required for applications such as drug screening.

SUMMARY OF THE INVENTION

The present invention provides an integrated sample handling and detection system that enables simultaneous preparation and performance of multiple assays of rapidly occurring, transient phenomena in a plurality of individual wells of a test plate; imaging of the assays with sufficient sensitivity and a high degree of accuracy continuously in real time over a period of time; and collection, storage, and analysis of the imaging data. The detection system and method of the present invention enable automated assays of large numbers of test samples quickly, efficiently, accurately, and economically.

The system according to the present invention is capable of accurately and simultaneously imaging a large number of potentially low-intensity, rapid, transient reactions. The system includes a robotic fluid handling system for automated delivery of liquids to wells of a test plate; a detection system for detecting the assays as they are performed; and a computer-controlled data acquisition and analysis system for controlling the operation of the entire system and for collecting and analyzing imaging data.

A preferred embodiment of the system of the present invention includes an apparatus for simultaneously performing a plurality of fluorescence assays including a plate containing a plurality of wells; a distributor for simultaneously distributing a predetermined amount of a liquid to each of the plurality of wells; an excitation source for simultaneously exposing the wells to excitation radiation; a detector for simultaneously detecting fluorescence emitted from each of the plurality of wells continuously in real time over a predetermined period of time; and a computerized controller for simultaneously controlling and coordinating the distributor, the excitation source, and the detector.

A second preferred embodiment of the system of the present invention includes an apparatus for simultaneously performing a plurality of signal-based assays including a plate containing a plurality of wells; a distributor for simultaneously distributing a predetermined amount of a liquid to a number of the plurality of wells; a detector for simultaneously detecting emissions emitted from each of the plurality of wells over a predetermined period of time; and a computerized controller for automatically and simultaneously coordinating the distributor and the detector.

A particularly preferred aspect of the system provides for increased accuracy of signal measurement by taking the ratio of the signals measured after excitation with light of a first wavelength and the signals measured after excitation with light of a second different wavelength. The ratio of two emitted light measurements can be a more accurate determination of the actual emitted light than single absolute measurements because the ratio cancels the effects of instrument drift, transient changes in instrument sensitivity and changes in cell volume or fluorescent indicator concentration, each of which may be mistaken for a change in the attribute being measured.

A third embodiment of the system of the present invention includes a plate containing a plurality of wells; a distributor for simultaneously distributing a predetermined amount of a liquid to each of the plurality of wells; a detector for simultaneously detecting optical emissions emitted from each of the plurality of wells over a predetermined period of time, wherein the detector includes a single imager for optically imaging the plurality of wells, the detector creating a time series of pixel images of each of the plurality of wells to determine an amount of optical emissions emitted from each of the plurality of wells over the predetermined period of time; a computer processor for acquiring, processing, and storing optical emissions data detected by the detector; and a computerized controller for simultaneously controlling and coordinating the distributor, the detector, and the computer processor.

A method according to the present invention comprises the steps of simultaneously distributing a predetermined amount of a liquid to a number of a plurality of wells; simultaneously exposing the wells to excitation radiation; simultaneously detecting fluorescence emitted from the plurality of wells over a predetermined period of time using a detector; processing fluorescence data detected by the detector; and simultaneously controlling and coordinating the distribution, excitation, and detection using a computerized controller.

Another method for performing simultaneous assays according to the present invention includes the steps of simultaneously distributing a predetermined amount of a liquid to a number of the plurality of wells; simultaneously detecting emissions emitted from the plurality of wells over a predetermined period of time using a detector; processing emissions data detected by the detector; and simultaneously controlling and coordinating the distribution and the detection using a computerized controller.

The method according to the present invention may be used, for example, for drug screening, wherein compound samples are assayed to identify compositions having the ability to activate, potentiate, or inhibit ion channels and/or receptors of a cell that, when activated, directly or indirectly contribute to a detectable change in the level of a predetermined ion in the cell. When used for drug screening, the method of the present invention includes the steps of providing each of a plurality of wells with viable cells having functional ion channels and/or receptors which, when activated, are capable of directly or indirectly causing a detectable change in a concentration of a predetermined ion in the viable cells, wherein the viable cells contain an amount of an ion-sensitive indicator sufficient to detect a change, if any, in the concentration of the predetermined ion; simultaneously distributing a predetermined amount of a putative ion channel-activating or receptor-activating, -potentiating or -inhibiting compound being tested for its ability to activate, potentiate or inhibit the ion channel or receptor to each of the plurality of wells; simultaneously detecting optical emissions emitted by the ion-sensitive indicator in each of the plurality of wells over a predetermined period of time using a detector consisting of a single imager for optically imaging the plurality of wells, the detector creating a time series of pixel images of each of the plurality of wells to determine an amount of optical emissions of the ion-sensitive indicator in the plurality of wells over the predetermined period of time; processing optical emissions data detected by the detector; and simultaneously controlling and coordinating the distribution, excitation, detection, and processing using a computerized controller.

When the method according to the present invention is used for screening compounds to identify compositions having the ability to inhibit or block ion channels and/or receptors of a cell (e.g., antagonist compounds), the test compound is added to the wells before or simultaneously with a known activator of the ion channels and/or receptors. The signal detected from the wells is compared to that detected from identical wells to which only the known activator is added in the absence of the test compound or from wells containing cells identical to the ion channel and/or receptor-containing cells except that they do not express the ion channels and/or receptors.

The method according to the present invention may also be used for screening cell lines to identify those that express functional ion channels and/or receptors. In these assays, known modulators of the ion channels and/or receptors are added to the wells containing the test cells, and the signal emitted by the ion-sensitive indicator is measured to determine if the intracellular ion concentration has changed in response to the addition of a known modulator to the cells.

The foregoing and other features, aspects, and advantages of the present invention will become more apparent from the following detailed description when read in conjunction with the accompanying drawings.

BRIEF DESCRIPTION OF THE DRAWINGS

FIG. 8D is a diagram of the pipette operation template editor displayed on user interface monitor 403 which is used by the operator to set pipette operation parameters of the fluorimetry system.

FIG. 8E is a diagram of the washing operation template editor displayed on user interface monitor 403 which is used by the operator to set washing operation parameters of the fluorimetry system.

DETAILED DESCRIPTION

The system according to the present invention will now be described with reference to the Figures. For purposes of the description of a preferred embodiment of the fluorimetry system of the present invention provided below, a microtiter plate having 96 wells is employed such that the fluorimetry system performs and analyzes up to 96 assays simultaneously. However, the fluorimetry system of the present invention is adaptable and may be utilized with different sizes of microtiter plates and deep well plates or plates having different numbers of wells to be simultaneously tested.

The system according to the present invention will be described with reference to cell-based assays wherein the fluid dispensed to cell-containing wells is a test compound or sample. It is understood that numerous other assays may be performed by the system according to the present invention, including cell-screening assays in which the cells in the wells are the test samples and a known reagent is added to the cells via the fluid-handling system.

The fluorimetry system according to the present invention includes three different interconnected and coordinated systems which operate simultaneously: a robotic fluid and plate handling system; an excitation and detection system; and a computer-controlled data acquisition and analysis system. Each of these three systems is described below in detail.

The Robotic Fluid and Plate Handling System

Figure 1:
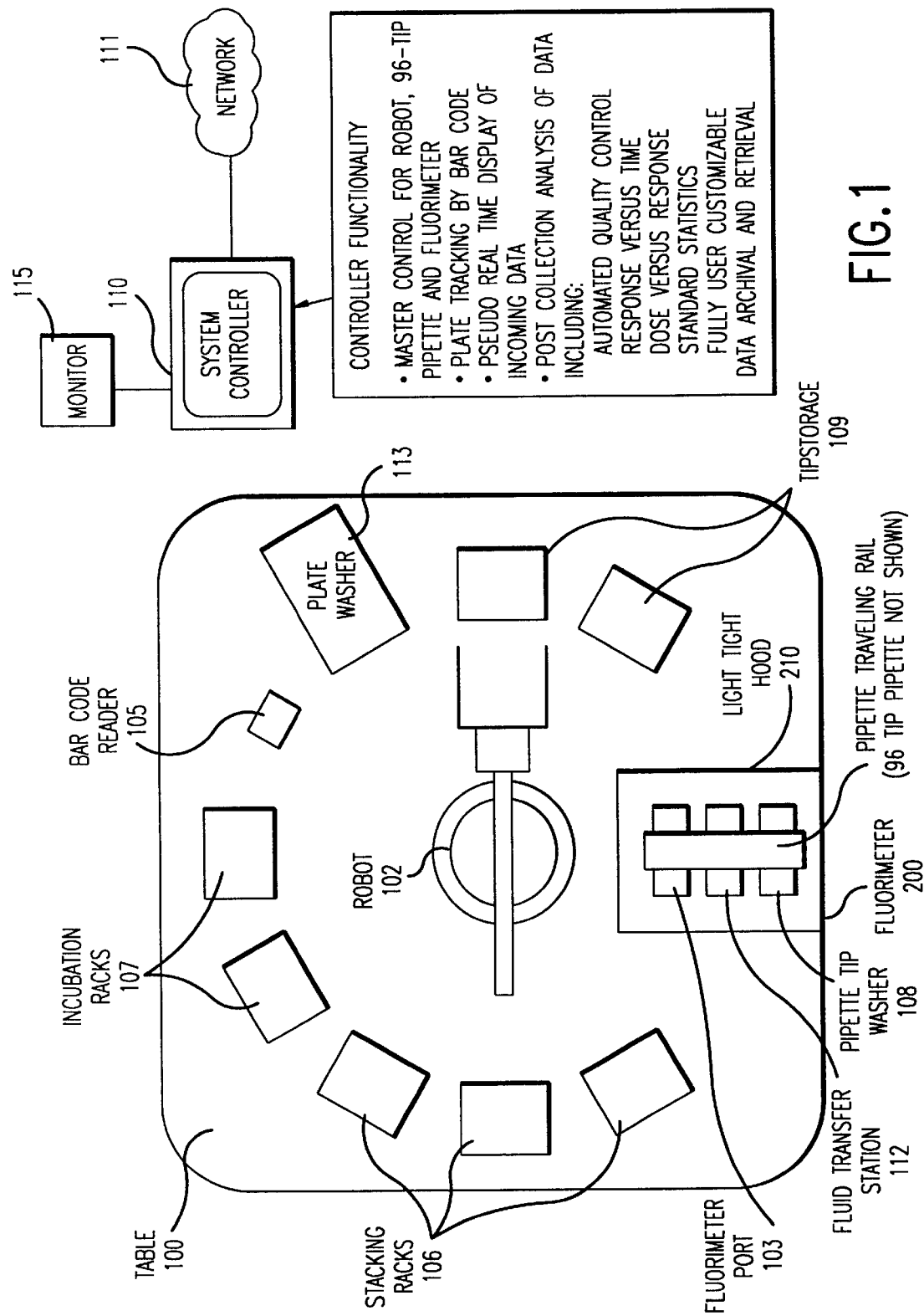
FIG. 1 is a system overview of the preferred embodiment of the robotic fluid and plate handling system according to the present invention including a diagram of a robot arm, a fluorimeter port, a plate washer, a tip washer and plate stacks, each of which is controlled by a system controller coupled to a network.
Figure 6:
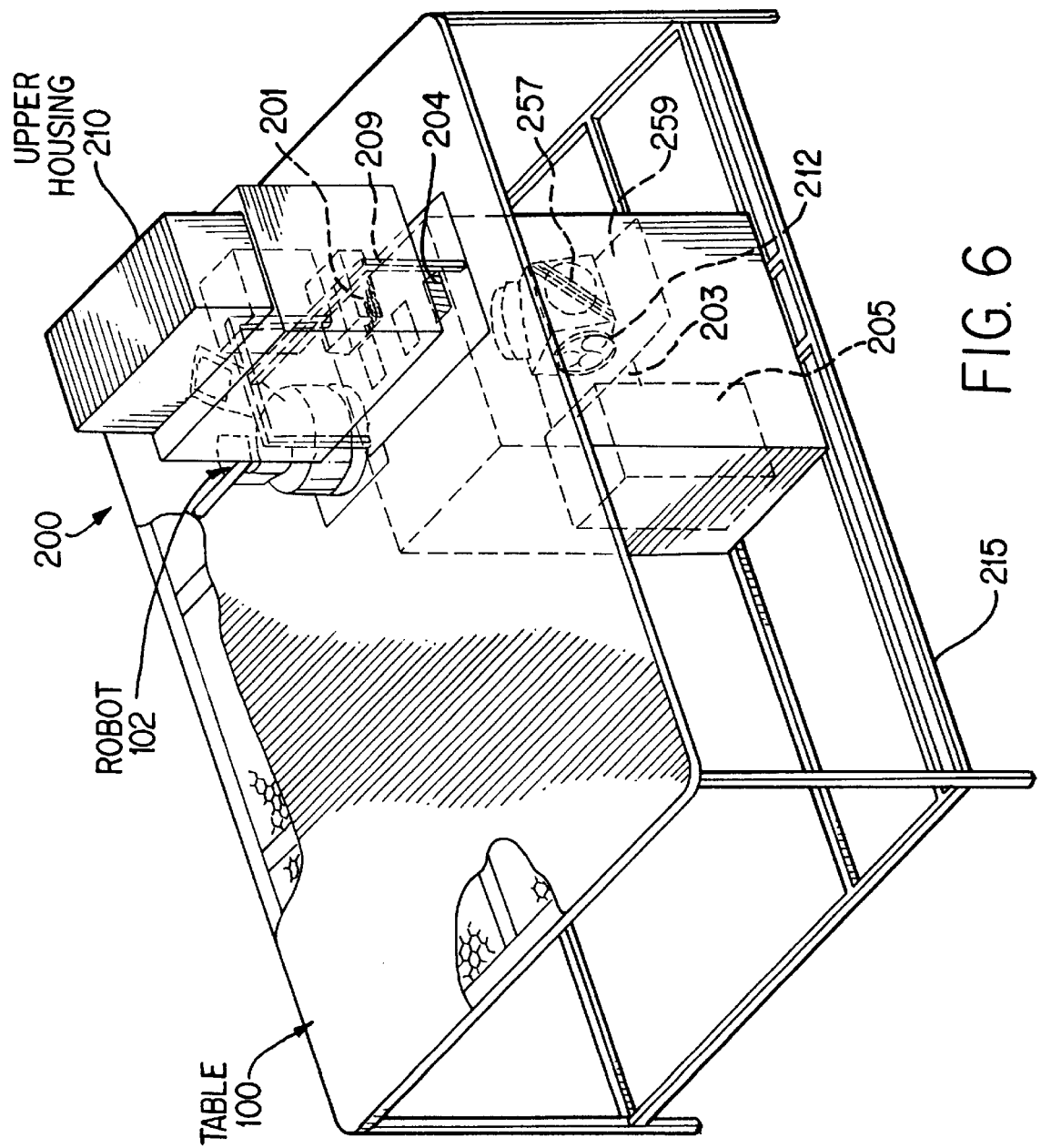
FIG. 6 is a diagram of the preferred embodiment of the fluorimeter including a fluid handling system, a pipetting head, a camera, and an excitation source.

As shown in FIGS. 1 and 6, the robotic fluid and plate handling system of the fluorimetry system of the present invention includes a table 100 onto which a robot arm 102 is installed. The robot arm is designed to have a single protrusion capable of picking up microplate-sized objects including microplates 204, deep well plates, and tip trays holding pipette tips used with the pipettes to distribute samples to the wells on a microplate 204.

The table 100 is provided with two ten-position plate incubators 107, provisions for stacking several piles of plates into stacking racks 106 and a plate washer 113. The table 100 further has a bar code reader 105 to read the identity of plates 204 which are each provided with bar code labels (not shown) for identification purposes. The fluorimetry system also includes tip plate storage racks 109 which store up to five tip plates each. The stored tip plates are accessible to the robot arm 102.

The liquid handling system of the present invention includes a 96-tip pipette head 202 (see FIG. 2A) which travels on a rail 209 to three positions. A base plate 211 (see FIG. 2A) supports the rail and is itself mounted on top of the fluorimeter assembly 200. The base plate also includes a fluorimeter port 103, a fluid transfer station 112 and a tip washing station 108. The transfer station 112 provides a tray in which plates can be placed by the robot prior to testing. The fluorimetry station 103 is provided by forming an opening in base plate 211 in which plates can be positioned by the robot for fluid aspiration and dispensing operations and through which the fluorimeter system can read the plate.

The plate tray in the fluorimetry station is different from the tray in the transfer station in that the plate tray in the fluorimetry station has an air cylinder which locks all plates in the same position. This positioning of the plates in the same position is important because the data acquisition and analysis system described below assumes that the wells of the plates are always in the same position. These expected positions may be entered and/or edited by the user through the Acquisition Template editor (shown in FIG. 8C) if the plate dimensions change.

The 96-tip pipette head 202 uses disposable tips which, when contaminated, may either be washed in the pipette tip washer 108 or discarded and replaced with new tips. The tips are held by a tip plate 201 (FIG. 2A) which may be removed from the pipette or replaced by the robot. The entire pipette and base plate assembly is covered by a light-tight upper housing 210. This housing may be automatically raised to allow robot access, or lowered to provide an environment which is free of ambient light during plate reading by the fluorimeter. Upper housing 210 may be removed for operator access.

Figure 2A:
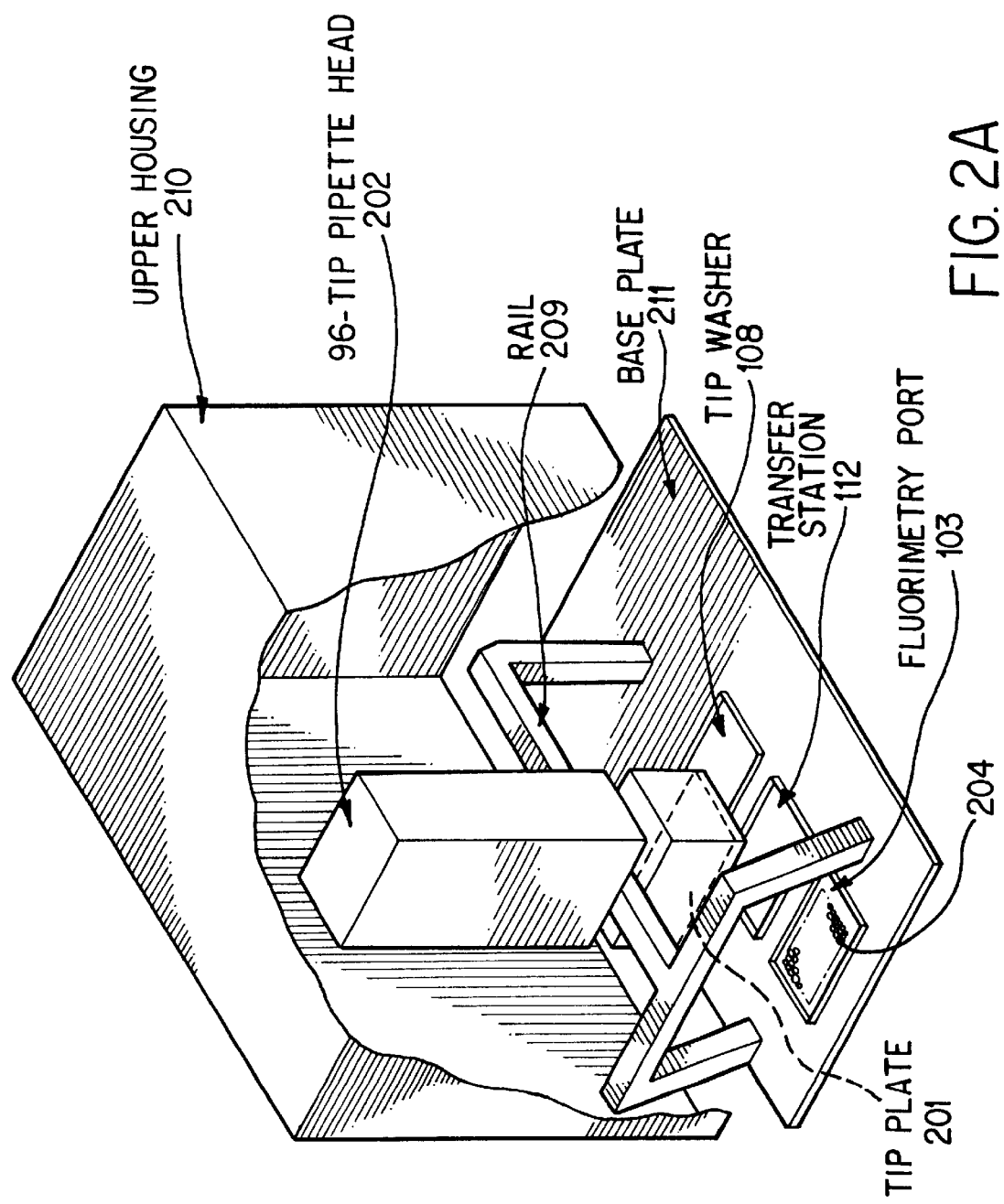
FIG. 2A is a diagram of the configuration of the fluid handling system of the fluorimetry system according to the present invention, including an outer housing, a 96-tip pipette head, a rail, and a base plate onto which test plates are positioned in different stations. The fluorimeter reads plates in one of the stations.

Operation of the fluid and plate handling system shown in FIGS. 1, 6 and 2A is accomplished by a system controller 110 (FIG. 1) which serves as the master control for the robot arm 102, the 96-tip pipetting head 202 and the fluorimeter 200. The system controller 110 tracks movement of the microplates 204 using the bar codes provided on the plates and read by the bar code reader 105. The system controller 110 can also display incoming data in "pseudo real time" (the display image may be slightly delayed from the real time image due to the limited communication channel bandwidth) on a monitor 115 attached to the system controller 110. The system controller 110 also performs post-collection analysis of data to provide automated quality control, response versus time displays, dose versus response displays, and other desired statistics. Additionally, the system controller 110 archives and retrieves the data received from the fluorimeter, the results of its analyses, and other desired data. The system controller may be operated individually or connected to a network 111 to allow for remotely controlled operation of the fluorimetry system, operation of multiple fluorimetry systems through a common network, or integration of the fluorimetry system with other types of systems desired by the operator. The system controller 110 will be described in further detail below with reference to FIGS. 4–9.

The automated fluid and plate handling system shown in FIGS. 1 and 6 provides an extremely flexible testing system capable of efficient testing of many test samples. The 96-tip pipetting head 202 contributes high throughput by providing test samples to each well in a 96-well microtiter plate 204 simultaneously. Plate washer 113 washes each well in a 96-well microplate 204 simultaneously. The robot arm 102 allows random access storage and movement of microplates 204 and tip plates 201 held by pipetting head 202, as well as incubation steps as desired by the operator of the fluorimetry system. Furthermore, the arrangement of system components is not limited to that shown in FIGS. 1 and 6 and may be modified to accommodate the testing needs of the individual operator without departing from the scope of the present invention.

Figure 4:
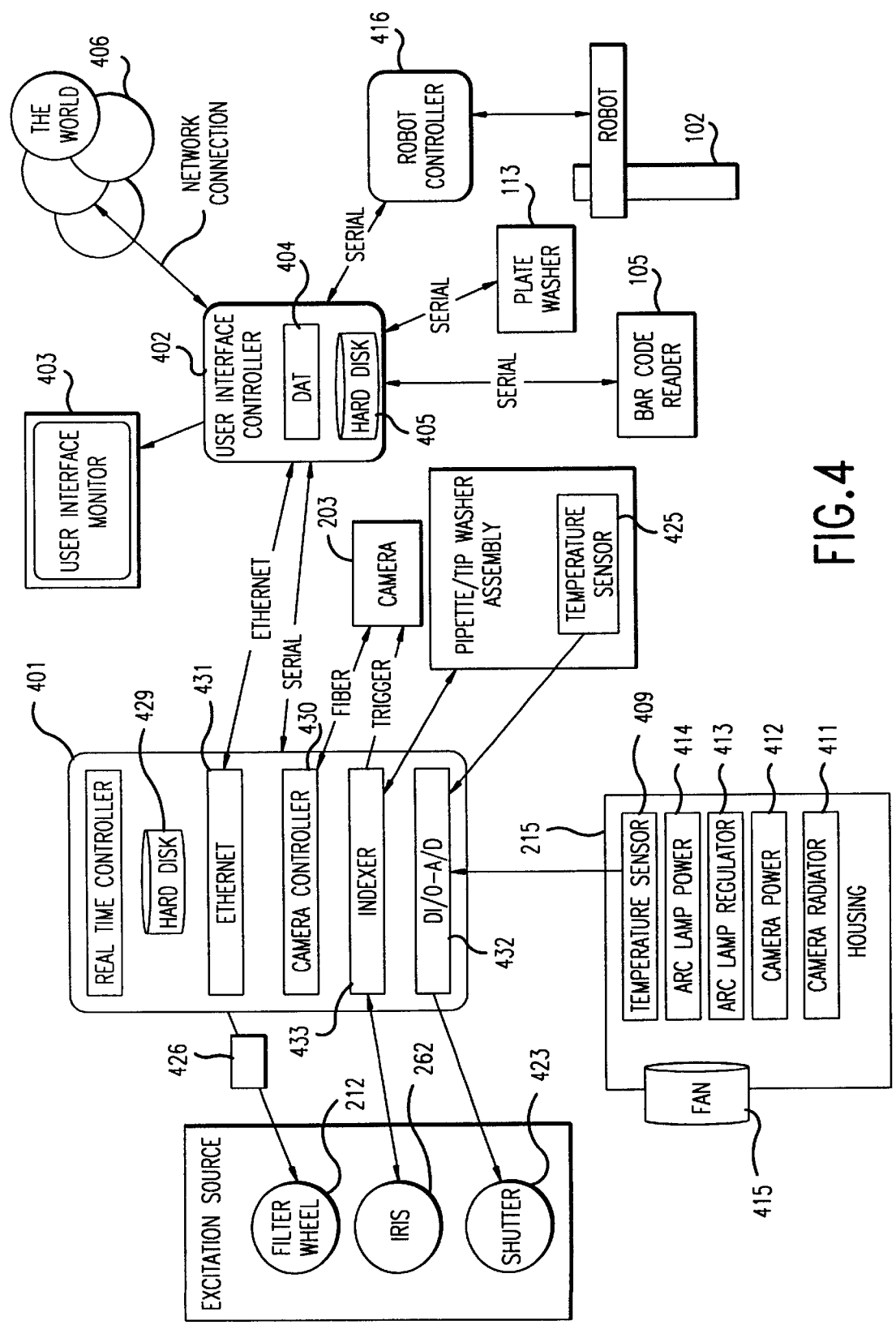
FIG. 4 is a diagram of the preferred embodiment of the computerized fluorimeter system control of the fluorimetry system of the present invention, including a real-time controller, a user interface controller, and a robotics controller.

The automated fluid and plate handling system of the present invention as shown in FIGS. 1 and 6 can be assembled using a robotic system manufactured by Zymark™ which includes the robot arm 102 and the robot controller 416 (see FIG. 4). The system controller 110 is multi-tasking, and may therefore be programmed to perform the simultaneous control features required in the fluorimetry system of the present invention. Specifically, the system controller 110 may be programmed to control operation of the robot arm, the pipettor (i.e., the pipette head and tip plates), and the fluorimeter simultaneously. The features of the computer-controlled data acquisition and analysis system will be described below in detail with reference to FIGS. 4–10.

The pipettor may be, for example, a 96-tip pipettor manufactured by Carl Creative Systems™ (CCS). The CCS pipettor may be integrated with the system controller 110 for simultaneous control of all operations of the fluorimetry system. However, any other suitable pipettor and robotics system may be used to assemble the fluorimetry system according to the present invention.

The Excitation and Detection System

The excitation and detection system in accordance with the present invention is designed specifically to address the requirements of performing high-throughput non-endpoint, or continuous, assays. These requirements are as follows. First, excitation and detection must occur through the bottom of the plate to allow a pipette to dispense reagents from above during the assays. Second, the detection system must have high sensitivity. Third, the system must have a sample rate of at least two samples per second taken for at least five minutes, and the ability to read as many sample wells simultaneously as possible. Other desired features include flexibility to read a variety of plate formats and sample quality observation capability.

In prior art systems, such as that described in International Application No. PCT/US92/11090, filed Dec. 18, 1992, and published on Jul. 8, 1993, a single optical fiber bundle is used such that one end of the bundle is positioned in close proximity to the bottom of the plate, for example, directly beneath a well to be tested. The bundle is split into two approximately equal halves, one connected to a filter on an excitation source, and one connected to a filter on a photomultiplier tube. This arrangement allows for excitation and detection through the bottom of the plate and high sensitivity, but does not allow for the required high sample rate or the ability to read as many wells as possible simultaneously. Further, modification of the prior art fiber optic system to allow the system to read 96 wells simultaneously is quite complicated. Additionally, the prior art fiber optic design cannot provide the features of flexibility or sample quality observation.

To overcome the drawbacks of the prior art, the detection system according to an illustrative embodiment of the present invention uses a camera which is positioned far enough below the plate to allow the excitation source to project onto the bottom of the plate from below, leaving the top of the plate unencumbered. The finite camera aperture of the camera is placed nearly a meter from the plate, resulting in a loss of approximately 99% of the light emitted from the plate (a rough approximation based on uniform spherical light distribution). This loss, while large, is roughly equivalent to the loss in the prior art fiber optic system which loses light despite the fiber optic's close proximity to the plate due to the effective numerical aperture of the fibers (a measure of the angle from which the fibers can accept light), the surface reflection off the face of the fibers, the fill ratio (the individual fibers are circular and have cladding which consumes area that could otherwise be used to gather light), and the loss of useful fibers which must be dedicated to providing excitation light.

The sensitivity of the detection system according to the present invention meets or exceeds the sensitivity of the prior art fiber optic system. Further, the system according to the present invention is able to simultaneously image 96 wells of a plate, and meets the high sample rate requirement using appropriate camera and real-time computer components described in detail below with reference to FIGS. 2A–C and 6.

The design of the excitation and detection systems in accordance with the present invention also includes the two other desired features listed above. First, the system has sufficient flexibility to read any desired plate format. The number of wells that can be read simultaneously is only limited by the camera's resolution. Also, by collecting high resolution images when the cells in the plate have been loaded with an indicator, for example, a fluorescent indicator, the system allows for observation of how uniformly the cells have attached themselves to the bottom of the wells of the plate. Second, by collecting a time series of images, the mechanical processes of reagent distribution within the wells may be observed. This information can be used to improve reagent delivery techniques and assay timing.

The excitation and detection system in accordance with the present invention will now be described with reference to FIGS. 2A–C and 6. According to a preferred embodiment of the fluorimetry system of the present invention, the fluorimeter 200 shown in FIGS. 2B and 6 comprises an excitation source 205 for inciting fluorescence of fluorescent dyes contained in the microplate wells. The fluorimeter 200 further includes an imaging system comprising a CCD camera 203 and emission filter 260 for detecting light emissions from the fluorescent dyes in the sample wells of the 96-well plate 204. These are contained within lower housing 215.

Figure 2B:
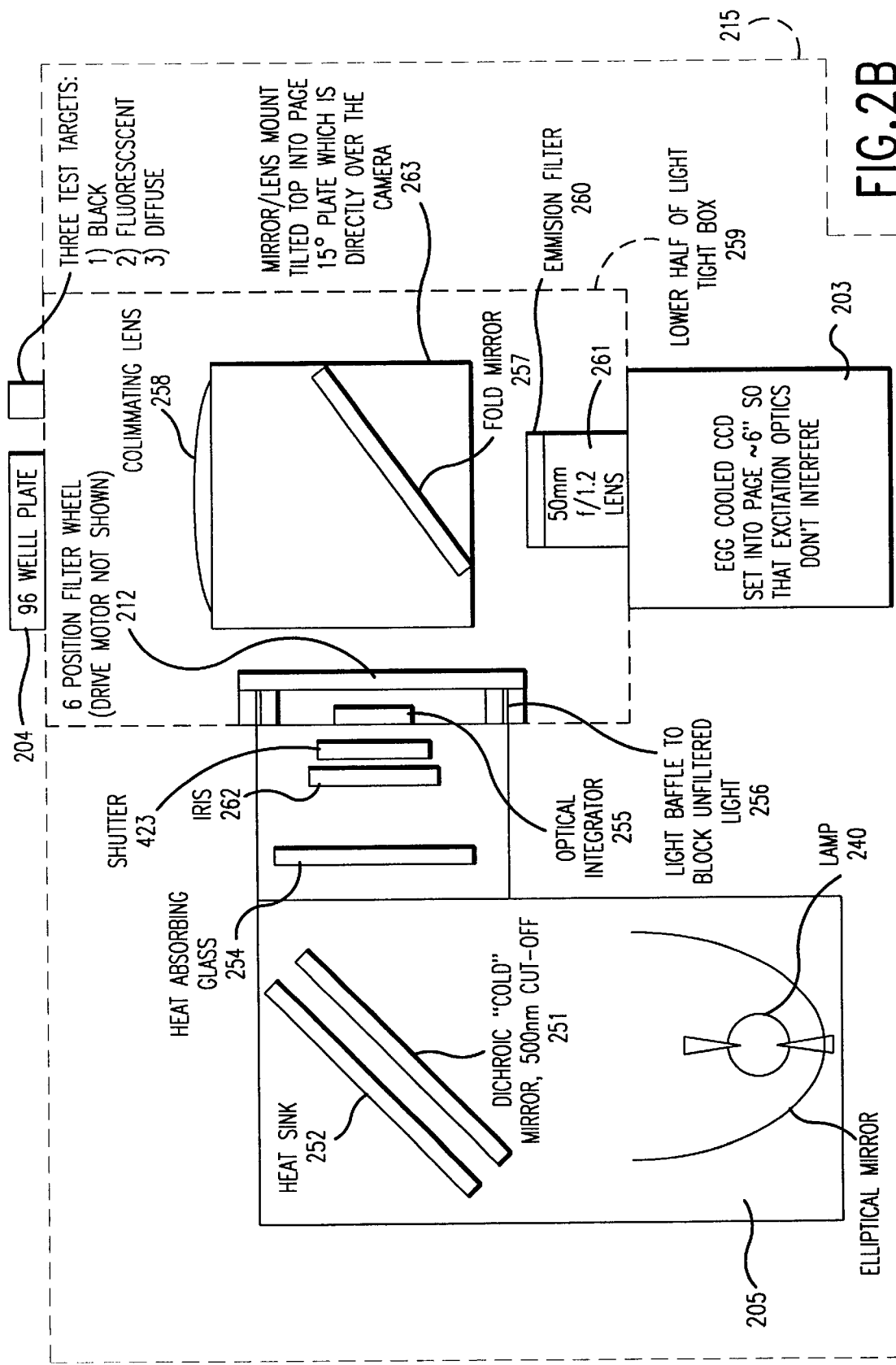
FIG. 2B is a diagram of the components of the excitation and detection system of the fluorimetry system according to the present invention, including a lamp, a dichroic mirror, a filter wheel, a fold mirror, a collimating lens, and a camera.
Figure 2C:
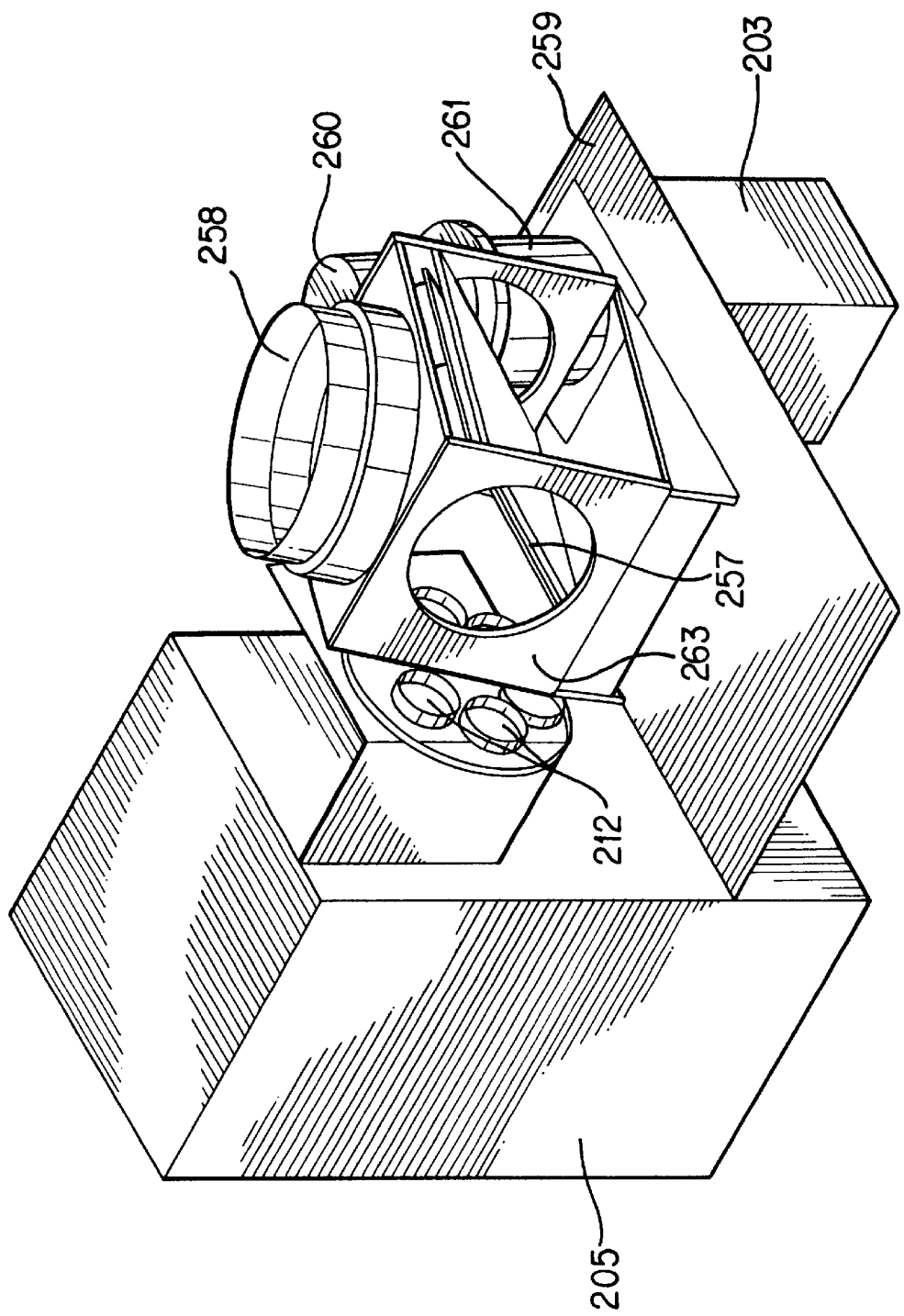
FIG. 2C is a diagram of the configuration of the excitation and detection system within the fluorimeter of the fluorimetry system according to the present invention, including an excitation source, a filter wheel, a collimating lens, and a camera.

The optical train of the fluorimeter 200 will now be described with reference to FIGS. 6, 2B and 2C. As shown in FIG. 2B, the excitation source 205 of the fluorimeter consists of a lamp 240, a projection system, a heat sink 252, a dichroic mirror 251, a heat absorbing glass 254, an iris 262, a shutter, 423, an optical integrator 255, and a six-position filter wheel 212. A drive motor (not shown) drives the filter wheel.

The lamp 240 is capable of providing a broad spectrum of light sufficient for both ratioed and non-ratioed fluorescence testing at any excitation wavelength. The lamp is preferably a Xenon arc lamp which provides a spike-free, broadband spectrum of light. A laser source may also be used. Commercially available lasers are not presently capable of producing an excitation of 385 nm which is used for ratioed fluorescence testing using the fluorescent indicator Fura-2. However, a laser such as a Krypton-Argon or Titanium:Sapphire laser or any other suitable type of excitation source capable of producing suitable excitation frequencies (e.g., 350 nm and 385 nm) as well as other frequencies necessary for ratioed fluorescence assays may be used without departing from the scope of the present invention. However, lasers of this type are currently very costly.

The projection system of excitation source 205 is designed to provide uniform illumination to the bottom of the 96-well plate 204 using the integrating lens 255, the fold mirror 257 and the collimating lens 258. To protect filter 212 from damage due to the energy of lamp 240, the projection system pre-filters the light from lamp 240 to a desired band. The light from the arc lamp 240 is pre-filtered using a dichroic mirror 251 whose reflection spectrum is broad enough to allow multiple individual wavelengths to be chosen with an interference filter such as 6-position filter wheel 212. The light energy not reflected by the mirror 251 is absorbed by a heat sink 252. Heat absorbing glass 254 further absorbs unwanted light. Excitation source 205 is positioned to provide the selected excitation frequency(ies) into a light-tight box 259. The amount of light reaching plate 204 is regulated by an iris diaphragm 262.

The plates 204 used for conducting detection assays with the fluorimeter must have clear bottoms such that the detector can receive the signals emitted from the wells through the bottom of the assay plate. For example, the plates may be made of plastic or quartz.

In general, care must be taken to select materials which do not interfere with the particular signal-generating technique utilized.

Filter 212 of excitation source 205 is, for example, a high-speed, six-position filter wheel including several standard interference filters with desired band-pass characteristics for particular tests. A drive motor (not shown) is operable to set filter wheel 212 in one fixed position, to rotate filter wheel 212 back and forth between two or more different filters, or to rotate filter wheel 212 continuously, depending on the type of filtering required to obtain the desired test results. For example, for ratioed tests requiring the use of two different bands of light, the filter wheel 212 is rotated back and forth between two adjacent filters, for example, ultraviolet filters, at a rate of four Hertz. For fixed filter operation, the filter wheel 212 is set such that a desired of the filters of the filter wheel 212 is positioned in the optical path.

Excitation of the fluorescent indicator in the wells may be constant excitation or rapidly repeated bursts of excitation frequencies, as long as the repetition rate of the excitation bursts is greater than the data acquisition rate of the detector, as will be discussed below.

The imaging system of the fluorimetry system according to the present invention comprises a CCD camera 203 that images the bottom of the microplate 204 using a commercially available lens 261 with an emission filter 260, such as a 50 mm f/1.2 lens. In accordance with one embodiment of the present invention, the lens 261 of camera 203 is chosen to provide high signal throughput. Although this may increase geometric distortions, such geometric distortions may be later corrected by the system controller 10. The lens 261 and emission filter 260 of the camera 203 are positioned within light-tight box 259. The mirror/lens mount 263 holding the fold mirror 257 and the collimating lens 258 are also contained within light tight box 259. The 96-well microplate 204 and several optional calibration targets are placed in an aperture at the top of the light-tight box 259, and the upper housing 210 (a light-tight hood) is lowered over the top of the plate to insure that no ambient light is present in the testing chamber formed by the upper housing 210 and the light-tight box 259.

The camera 203 is, for example, a standard front-illuminated, cooled CCD camera having 40% quantum efficiency and a system noise of 4–5 e- at 50 kHz and 5–7 e- at 100 kHz, and 18 bits dynamic range. The camera 203 has, for example, 8 MB of random access memory to store several minutes worth of data. A camera with higher sensitivity and lesser dynamic range, such as a back-illuminated, thinned and cooled CCD with 80% quantum efficiency and a system noise of 6–7 e- at 50 kHz and 35–40 e- at 400 kHz and 12 bits dynamic range may also be used. An intensified CCD camera may be used at the expense of still lower dynamic range and higher noise. A 30 Hz "video" camera may be used with an intensifier if higher speeds are required. In this case an intensifier would have to be used or sensitivity would suffer.

Figure 3A:
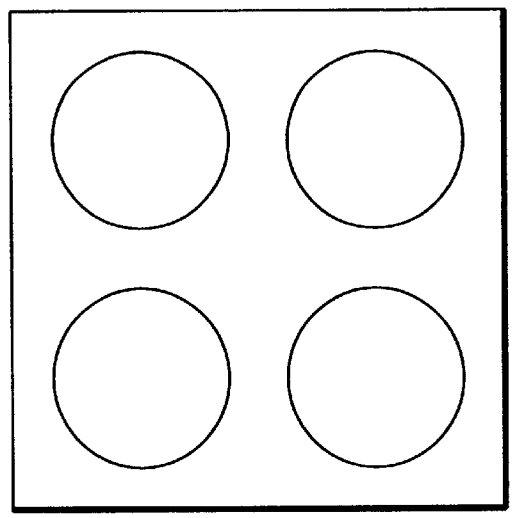
FIG. 3A is a diagram illustrating one possible read-out pattern for data representing a fluorescent image detected by the CCD detector and read out to the fluorimeter acquisition and processing unit.
Figure 3B:
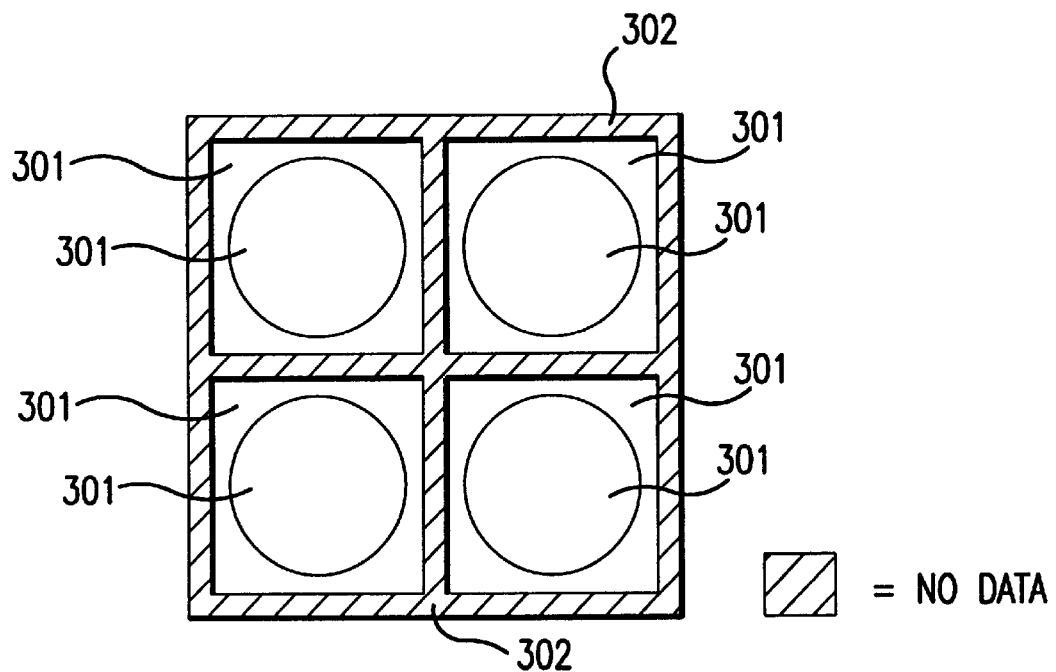
FIG. 3B is a diagram illustrating another possible read-out pattern for data representing a fluorescent image detected by the CCD detector and read out to the fluorimeter acquisition and processing unit.

The camera 203 is configured to provide flexibility in the manner in which the charges (hole-electron pairs) collected on the surface of the semiconductor created by incident photons received from fluorescent emissions from the wells of the microplate 204 are "shifted" out to the digitizer and then to the camera controller 430 (see FIG. 4). The CCD camera 203 may be configured to read and shift out collected data sequentially pixel-by-pixel and line-by-line (the format for operation of standard video cameras) to form a complete image of the microplate 204 as shown in FIG. 3A (showing the image of four sample wells on the plate 204). The camera 203 may also be configured to read only certain pixels within certain rows, for example, read the first five, skip the next ten, read the next five, skip the next ten, and so on. The same pattern is used to shift the data bits out to camera controller 430, creating a pattern of rectangular areas of image data corresponding to rectangular areas of the plate 204 as shown in FIG. 3B, wherein areas 301 are the areas for which data is read out of the CCD and area 302 is the area for which data is not read out of the CCD. The flexible readout feature of camera 203 eliminates the need for collection, processing and storage of unnecessary image data collected by the camera 203. Further, the camera may add rows or columns on the CCD prior to digitizing and reducing the quantity of data read per frame further.

The camera 203 can operate in two different modes, depending on the type of data required by the operator. In a first mode of operation, each single frame image taken of the reactions in the plate 204 is processed such that all pixels corresponding to an individual well are added to generate a number for that well indicating the total number of photons received by the camera 203 for that well. This process is performed for all of the wells on the plate 204, resulting in 96 numbers, one for each well. The operator may also designate other areas as calibration targets and receive additional numbers corresponding to each of these assay wells, as shown in FIG. 3B. This mode of operation allows for storage of data corresponding to a large number of frames because only four bytes of data corresponding to each well are stored for each frame.

In the second mode of operation, all of the pixel data collected by the camera 203 is retained and stored. In this mode of operation, a much larger quantity of data is stored for each frame. Therefore, the camera 203 can store data corresponding to fewer frames.

Figure 8A:
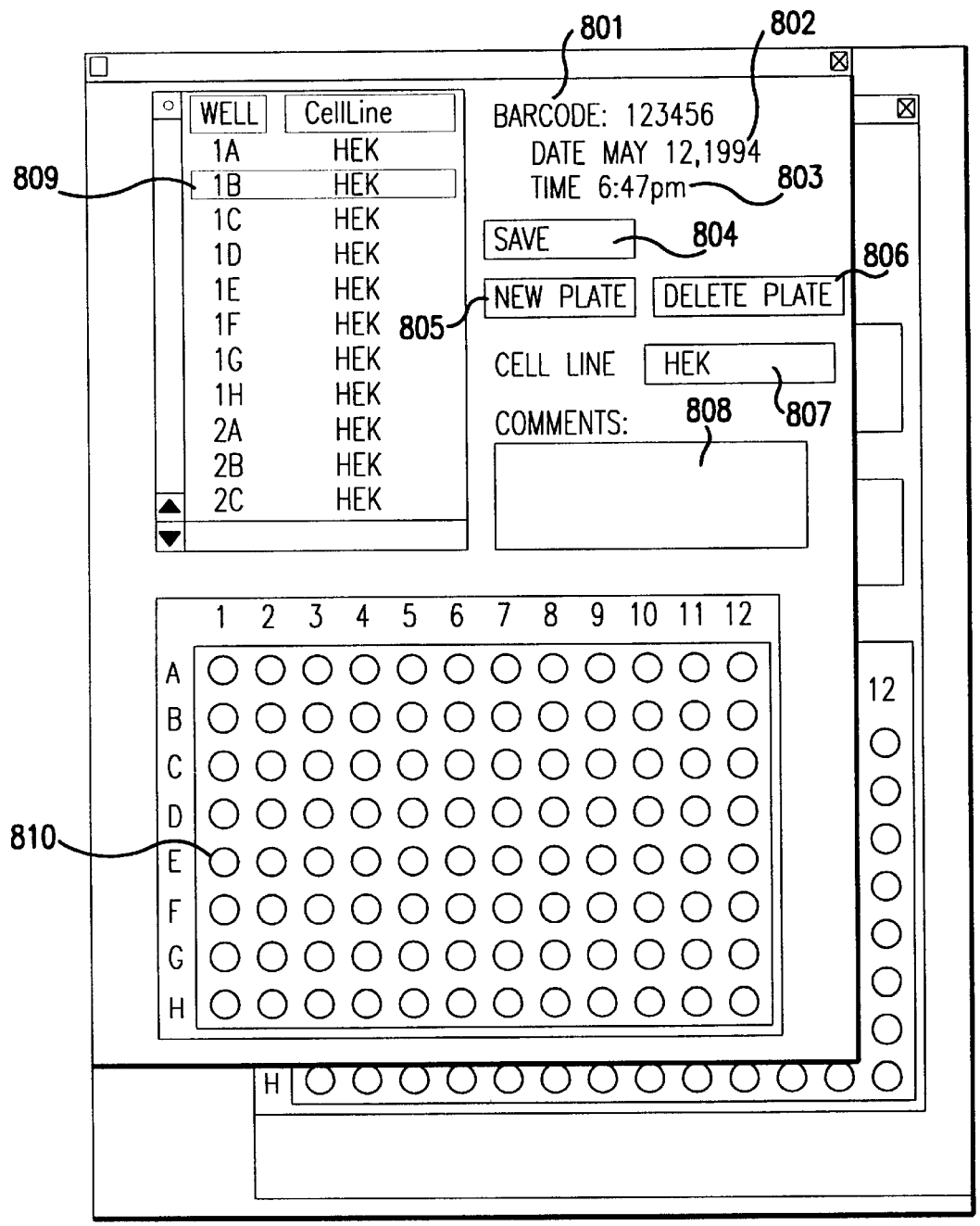
FIG. 8A is a diagram of the data entry tool displayed on user interface monitor 403 shown in FIG. 4 which is used by the operator to enter assay data.

A user interface may also be provided whereby the mode of data acquisition of the camera 203 may be modified by the operator to provide a desired frame read-out format. An example of this type of modification tool is shown in FIG. 8C.

The Computer Controlled Data Acquisition and Analysis System

The system controller 110 will now be described in detail with reference to FIGS. 4, 5, and 7–10. As illustrated in FIG. 4, the computer-controlled data acquisition and analysis system of the preferred embodiment of the fluorimetry system according to the present invention, or the "Fluorimeter System Control," comprises a real-time controller 401, a user interface controller 402, and a robotics controller 416. These three controllers automatically control, coordinate and monitor the operation of the different components of the fluorimetry system in order to enable automatic, efficient and accurate testing of a large number of test samples.

With reference to FIG. 4, the central component of the fluorimeter control system is the real-time controller 401. The real-time controller 401 comprises a hard disk 429, a camera controller 430, an ethernet™/PCNFS interface (431), and a digital input/output and analog/digital converter (DI/O and A/D) component 432. The hard disk 429 temporarily stores data collected from the components of the fluorimetry system. The camera controller 430 receives data from the camera 203, transmits control data to the camera 203 through a fiber optic cable, and sends control signals to motor controller 426 of the filter wheel 212 via a serial connection. The motor controller 426 also sends trigger data to the camera 203. The ethernet™ interface enables network communications between the real-time controller 401 and the user interface controller 402. The DI/O and A/D component 432 receives inputs from other components in the fluorimetry system including temperature data from temperature sensor 409 within lower housing 215, event triggers from the robotics controller 416, and temperature data from the temperature sensor 425. The DI/O and A/D component 432 also transmits position control data to the shutter 423 of the arc lamp 240. The indexer 433 controls all pipette motion including dispense, aspirate, motion along the rail, vertical motion of the pipette itself, and tip plate changing. The indexer also controls the position of the iris 262.

The user interface controller 402 of the fluorimeter control system shown in FIG. 4 includes a hard disk 405 for storing all data necessary for the operation of the fluorimeter control system and test results data as well as a digital audiotape backup system 404 (DAT). A user interface monitor 403 is attached to the user interface controller 402 to enable the user to monitor the activity of the fluorimeter and to enter commands to control the operation of the system. The user interface controller 402 may also be connected to a network 406, for example, ethernet™ or Novell™ or any other desired system, to allow for communication between the fluorimeter system control and other remote computer systems.

The user interface controller controls and schedules all of the other devices and controllers including the real-time controller and the robot controller. It is this computer that orchestrates the entire data collection and material handling process.

The lower housing 215 of the fluorimeter system contains the light-tight box 259 containing most of the optical train of the fluorimeter (described with reference to FIGS. 2B and 2C) to prevent ambient light from affecting the images detected by the camera 203. The lower housing 215 also contains a temperature sensor 409, a camera power supply 412, a camera radiator 411, an arc lamp power control 414, an arc lamp regulator 413, and a fan 415.

Figure 5:
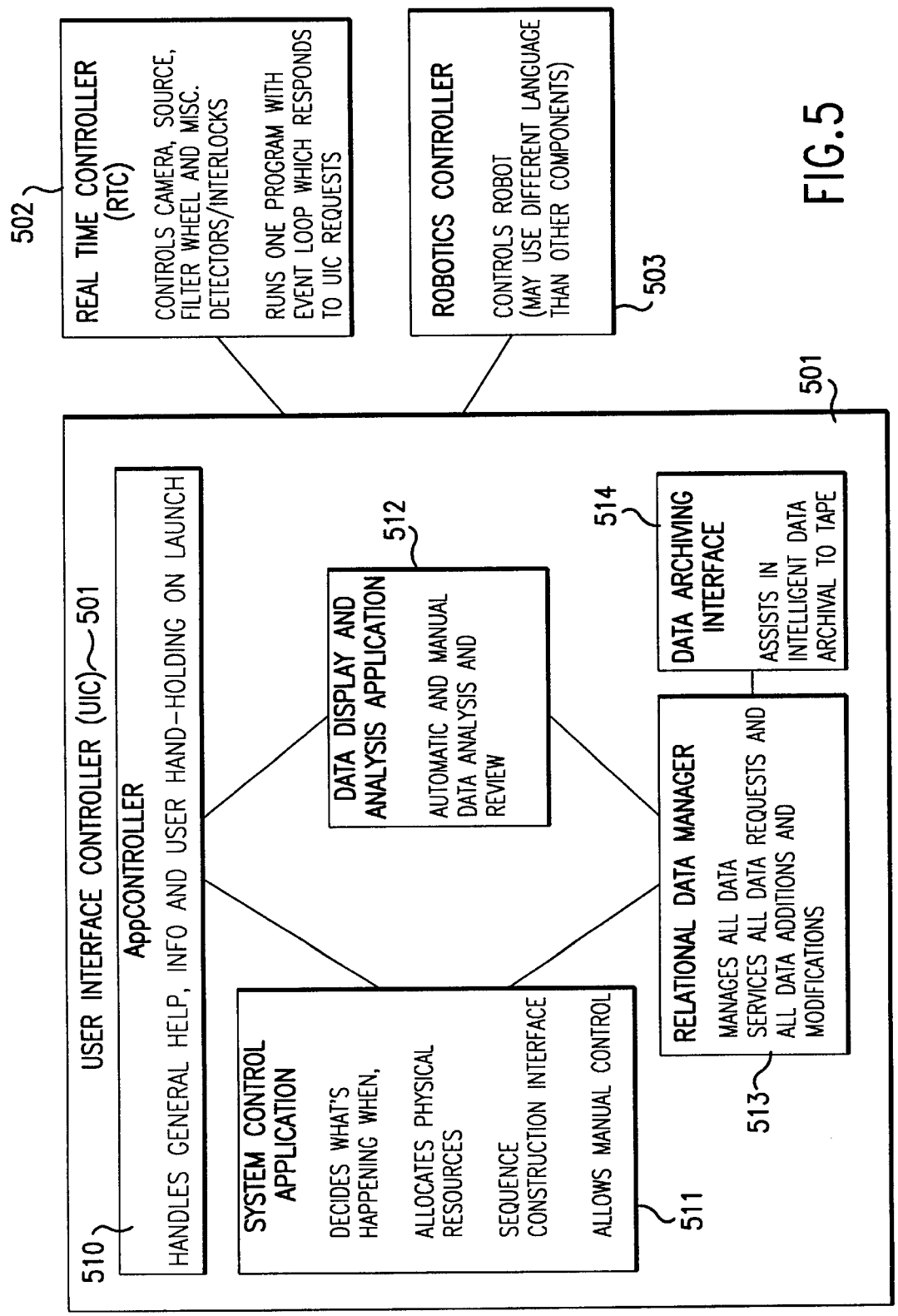
FIG. 5 is a diagram of one possible fluorimeter software system for operating the computerized control system of the fluorimetry system according to the present invention, including an overview of the software for the user interface controller (UIC), the real-time controller (RTC), and the robotics controller.

FIG. 5 provides a diagrammatic overview of one possible software system that may be used in the fluorimeter system control of FIG. 4. As illustrated in FIG. 5, this fluorimeter system software includes programs for the user interface controller (UIC) 402, the real-time controller (RTC) 401, and the robotics controller 416. However, any suitable software system may be used to operate the fluorimetry system of the present invention without departing from the scope of the invention. Furthermore, the fluorimeter and the liquid handling system may be stand-alone systems and may also be integrated into a network.

The UIC program 501 includes several applications. An application controller 510 (AppController) is provided for handling general help, information and user training functions. A system control application 511 controls the sequence of functions of the fluorimetry system according to the present invention, allocates physical resources to maximize efficiency and/or accuracy of the fluorimetry system, forms a sequence construction interface, and provides a manual control option for the fluorimetry system. The system control application is described in further detail below with reference to FIG. 7. A data display and analysis application 512 provides automatic and manual data analysis and review of data received from the components of the fluorimetry system, primarily data received from the camera 203 of the fluorimeter 200. A relational data manager 513 may be provided to manage all data and service all data requests, data modifications, and data additions. A data archiving interface 514 may be used to assist in intelligent data archival to a digital audio tape (DAT 404) or other data storage means.

The real-time controller (RTC) program 502 includes applications to control operation of the camera 203, the excitation source 205, the filter wheel 212, the pipette 202, and other detectors and interlocks within the fluorimetry system. The RTC runs one program with an event loop that responds to requests transmitted from the UIC.

The robotics controller program 503 controls the operation of the robot arm 102. The robotics controller program 503 provides control commands to the robot based on inputs received from the UIC 402.

Figure 7:
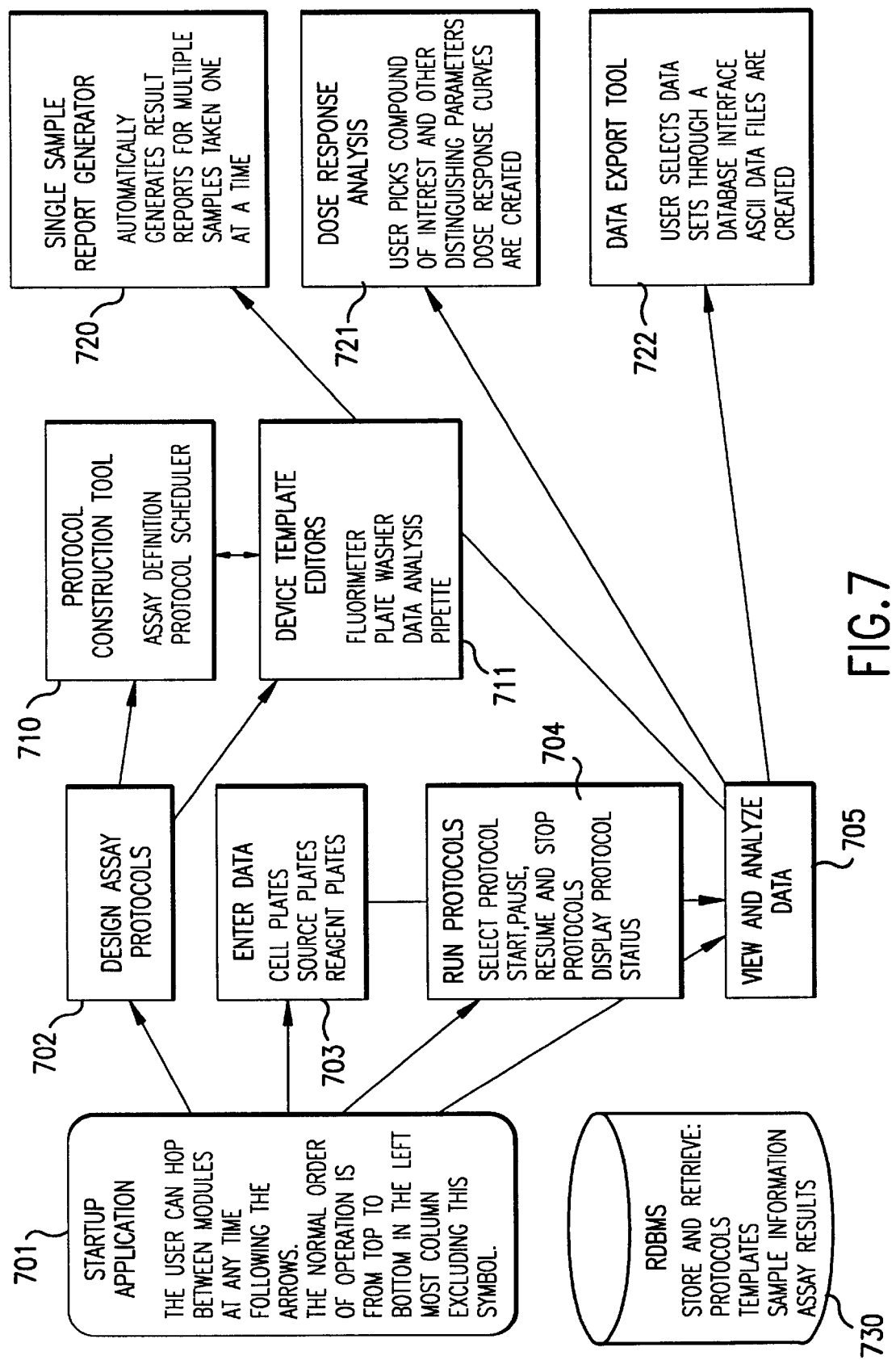
FIG. 7 is a diagram of the user operation overview of the user interface controller (UIC) of the fluorimetry system.

The system control application 511 of the UIC program 501 will now be described in further detail with reference to FIG. 7. FIG. 7 provides a user operation overview illustrating the operations to be performed by the operator in controlling and monitoring operation of the fluorimetry system. The operator controls and monitors the operation of the fluorimetry system on user interface monitor 403 shown in FIG. 4.

The start-up application 701 of the user operation system allows the operator to access a "design assay protocols" module 702, an "enter data" module 703, a "run protocols" module 704, and a "view an analyze data" module 705. The "design assay protocols" module 702 allows the operator to set the parameters for the operation of the fluorimetry system using a protocol construction tool 710 (an assay definition protocol scheduler) and device template editors 711.

In one embodiment, the system according to the present invention is configured to use the assay programming and scheduling tools from Zymate™ (the robot manufacturer) or similar software from other sources.

In a preferred embodiment of the system according to the present invention, the system is configured to use assay programming and scheduling software as will now be described.

Current systems require the user to program assays in terms of plate and well positions, not plate and well contents. That is, plate operations are defined by which rack position the plates should be fetched from or put into, while data operations are defined by specific well numbers. For example, if a standard spread sheet is used to process data automatically, it must have fixed input positions for its operations. This methodology requires users to always perform assays in the same way. That is, the system must be loaded with plates in the same positions each time and materials must be loaded into the plates the same way each time.

In accordance with the present invention, a relational database and the barcoding of all plates used in the system are implemented to avoid these restrictions. In this system, the user enters information about the contents of all the plates, reagent, cell and test compounds into the database along with the plate's barcode. When the user begins to run a set of assays, the robot immediately scans all plate storage racks and records which plates are in which positions by barcode. It records any empty slots for use as incubation stations. Because the controlling computer is tied to the database, the controlling computer knows what plates are in the system by plate contents as well. This allows the user to specify an assay by function. Thus, instead of programming the robot to get a plate from rack two, position three, for example, the user programs the robot to get the next test reagent plate, or a plate with lysis buffer.

The automatic data analysis tools take advantage of the relational database to combine data in any method desired, independent of plate or well position. For example, to obtain a dose response curve, all tests run on a single compound in different concentrations must be combined. In known methods, the user must load the plates in the order the analysis tools expect them. In the preferred system, the different concentrations may be on any plate in any position, run on any day. The database automatically finds the correct data for the data analysis tool. Further, the user can combine data in different ways at any time, even years after the data was collected. The user can include all kinds of information about the plates used, and any of the parameters can be used for searches and statistics at later date. The Protocol Construction Tool 710 is a user interface to implement this functional programming scheme. This tool helps the user design a protocol which defines a single complete assay in biological terms.

In a preferred system, a scheduler is created to run multiple assays. Current schedulers take a single assay program, in plate position terms, and run it multiple times, incrementing a user variable to advance the plate positions. In a first type of known optimization, the start time of subsequent assays is optimized to overlap operations, when possible, in a simple way. For example, if an hour-and-five-minute long incubation is called for twenty minutes into an assay, the scheduler will start three assays while the first is incubating. This optimization works well, but does not extend well to multiple systems working together.

There exists a second known type of scheduling optimization which, if implemented solves the multiple system collaboration problem. This optimization uses the fact that assay systems contain multiple independent devices. In the preferred system, the fluorimeter, plate washer, and robot can all be used simultaneously. A typical optimization within an assay is to start a plate washing, and then, during the wash, move a source plate into the transfer station of the pipette. By the time the washer is finished, the robot is ready to fetch it and move it to the fluorimeter station for a transfer operation.

While this second type of optimization might seem practical, the optimizations may, in fact, cause the simple optimization discussed previously to be worse. Suppose that a protocol is defined with ten minutes of set up followed by 21 minutes of incubation. In the simple mode, two assays are started during the first incubation period. Suppose now that in the single assay definition the user optimizes by doing a two minute plate wash during that incubation. There are now only 19 minutes free which means that one instead of two assays are started during the incubation. In this example case, two minutes are saved for a single assay, but at least ten minutes are lost when multiple assays are run.

In accordance with the present invention, this problem is solved by permitting the user to choose when to do assay optimizations with the scheduler. The user is presented with multiple tracks in which to do operations. These tracks may be tied together at certain critical points. In the example set forth above, the plate wash operation is in a first track while the robot's fetch and move operation of the plate to the transfer station is in a second track. The transfer operation of transferring the plate to the fluorimeter port is also in the first track, but a tie point is placed before the transfer operation. The tie point causes the scheduler to make sure that the operations in the second track are finished before the transfer operation begins. The user may provide as many tracks as there are devices, or may simply provide a single track.

The preferred scheduler allows the user to schedule multiple copies of an assay, or different assays in any order desired (because of the unique database arrangement discussed above). The scheduler automatically performs a simple optimization and reports the total time to run all assays. The user may then rearrange multiple track optimization and observe the effects on total run time. The user uses this technique to itteratively approach an optimal combination of optimization techniques. The optimization may also be performed automatically by computer.

To extend the preferred scheduler to control multiple systems, more tracks may be added, and single system assays may be combined into a single large assay. The multiple tracks may be used for whole systems as well as subsystems. The tie points are used between systems just as between devices.

All of the protocol design and scheduling tools described above are created with graphic user interfaces and run on the user interface controller or a networked machine. They are designed to graphically represent the tracks and schedule. The user drags tokens representing operations from lists into the multi-track protocol definition. The lists correspond to different devices. The items in the list are tokens representing predefined templates for that device. The user may edit the templates with the push of a button.

Figure 8B:
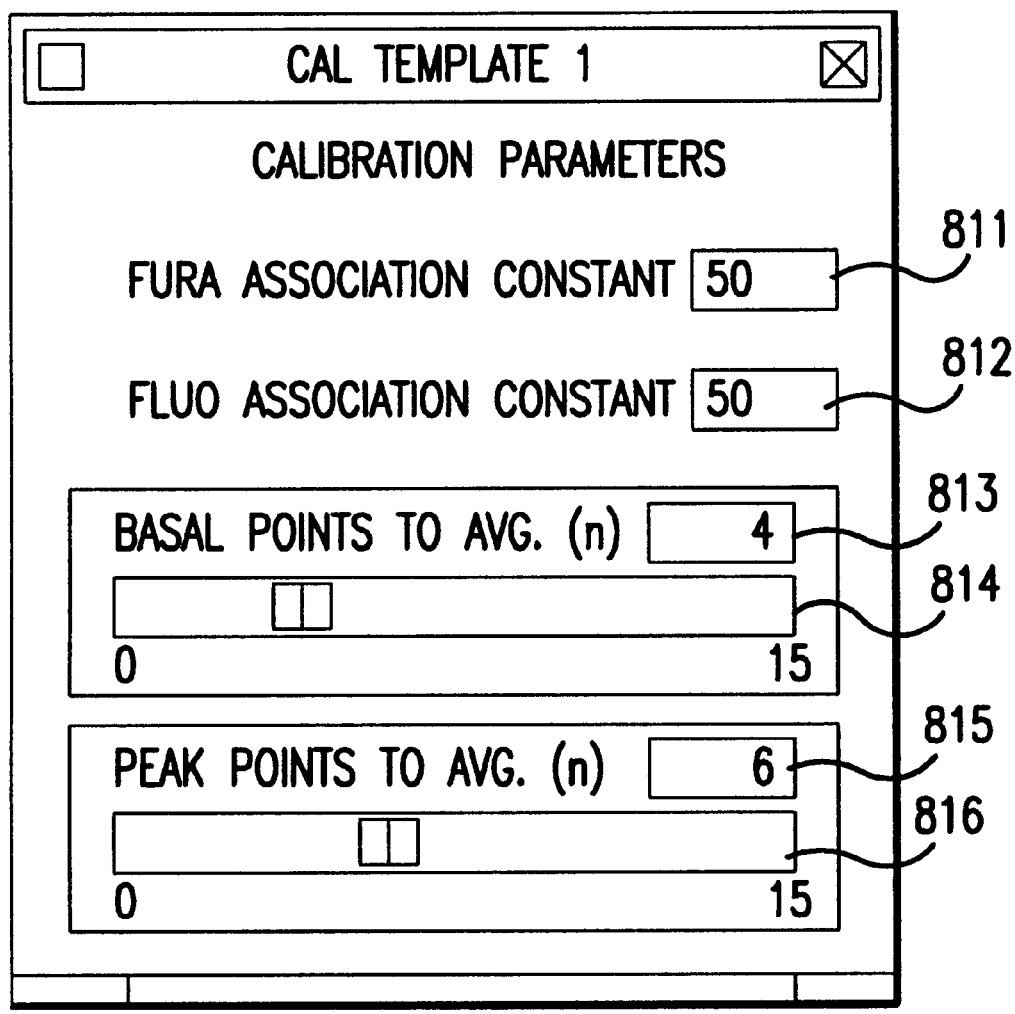
FIG. 8B is a diagram of the calibration template editor displayed on user interface monitor 403 which is used by the operator to set the calibration parameters of the fluorimetry system.
Figure 8C:
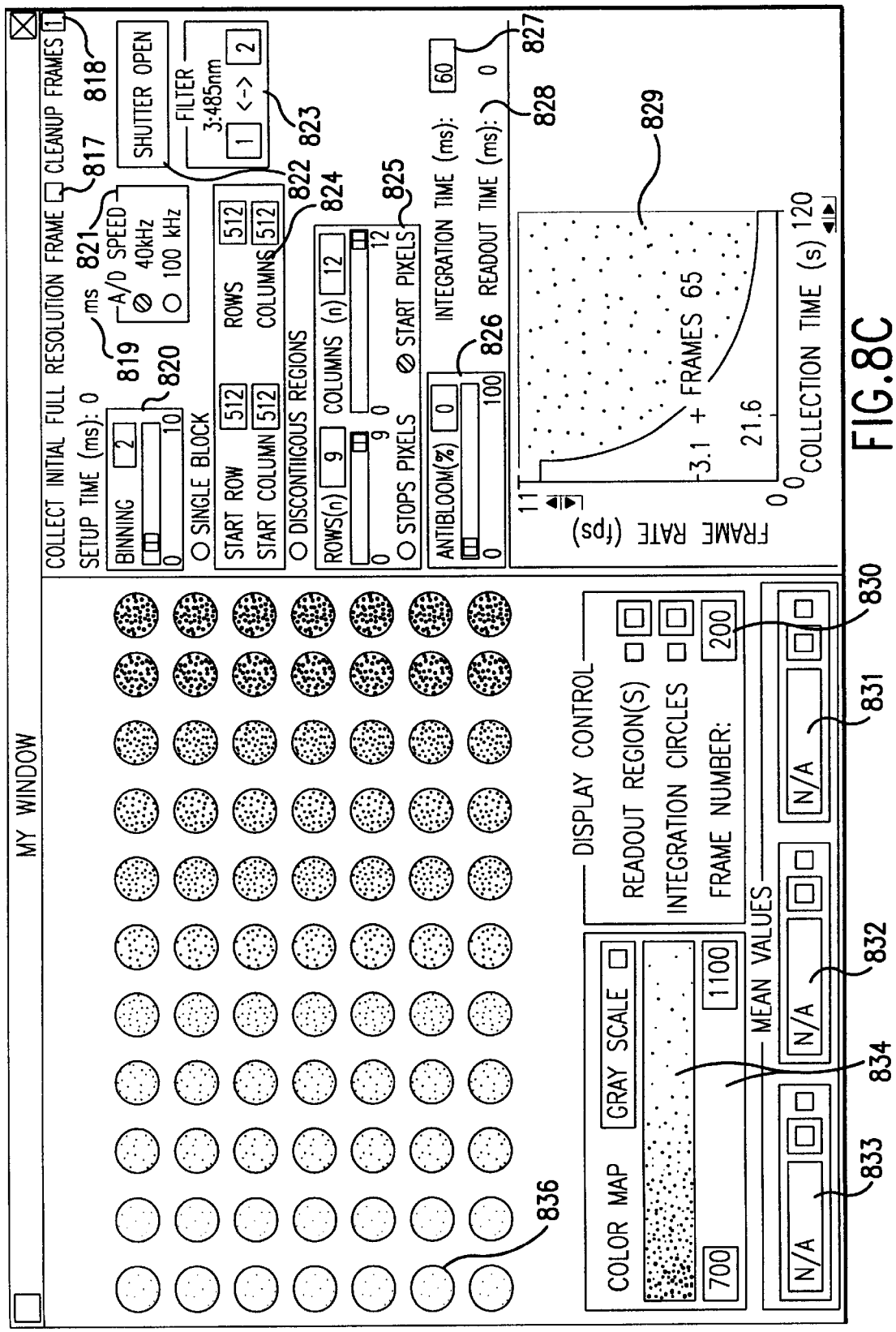
FIG. 8C is a diagram of the acquisition template editor displayed on user interface monitor 403 which is used by the operator to set parameters for data acquisition by the fluorimetry system.
Figure 8E:
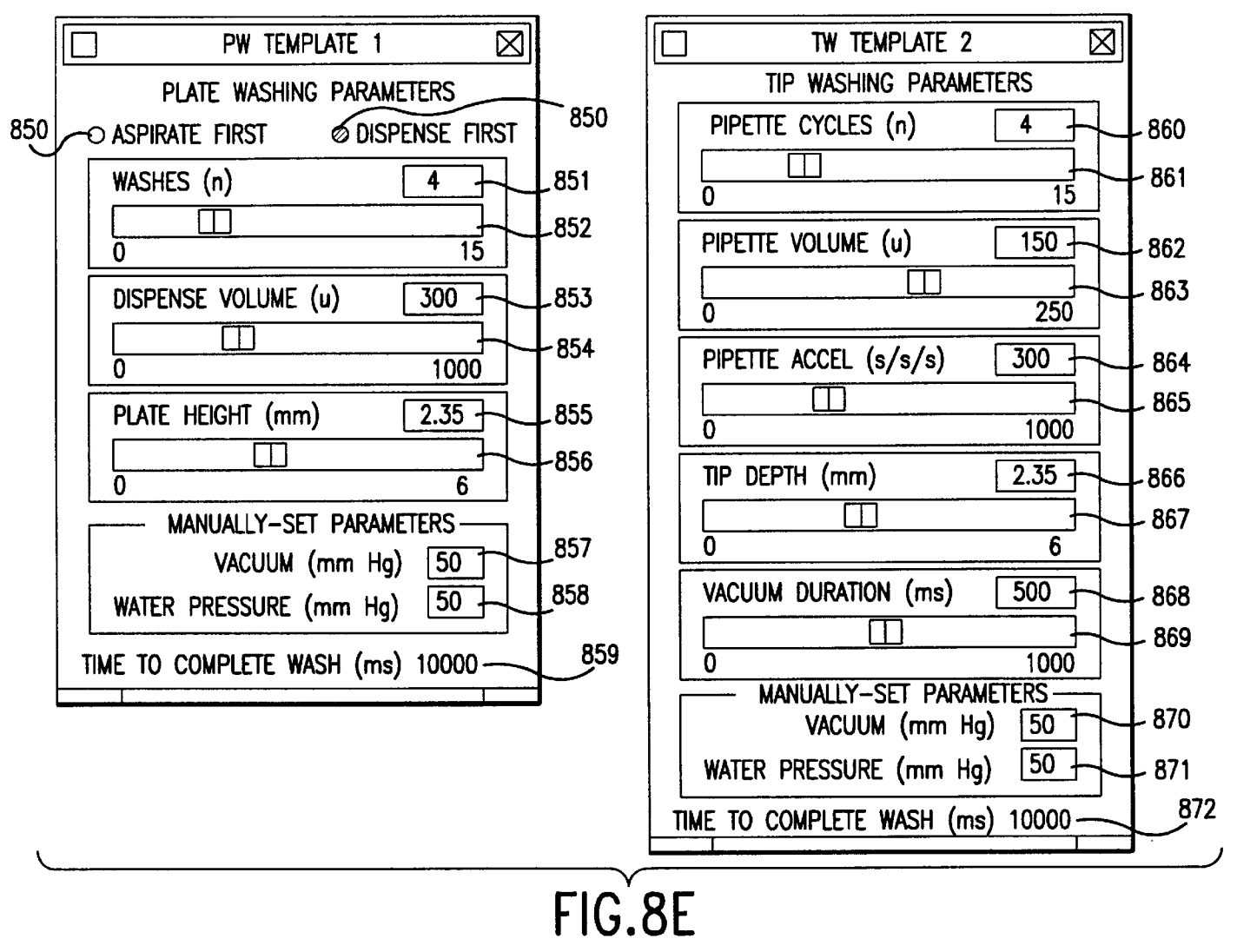

Several of the template editors are illustrated in FIGS. 8B–E. FIG. 8B illustrates a calibration template editor which enables an operator to set the calibration parameters for the assays to be performed by the fluorimeter. FIG. 8C shows an acquisition template editor that enables an operator to set data acquisition parameters for the fluorimeter. FIG. 8D illustrates a pipette operation template editor that enables an operator to set the parameters for pipette aspiration and dispensing during testing. FIG. 8E shows a washing operation template editor that enables an operator to set the parameters for plate and tip washing during operation of the fluorimetry system. Use of these screens will be described in further detail below.

With reference to FIG. 7, the "enter data" module 703 of the user operation system allows an operator to enter data identifying the cell plates (plates containing cells for use in the assays), source plates (e.g., containing the compound(s) to be tested in the assays), and indicator plates (e.g., containing the fluorescent indicator to be used in the assays) to be used by the fluorimetry system during testing. For example, FIG. 8A illustrates an example of a data entry tool displayed on user interface monitor 403 which enables an operator to enter information concerning the cell plates, source plates, and indicator plates.

Figure 9A:
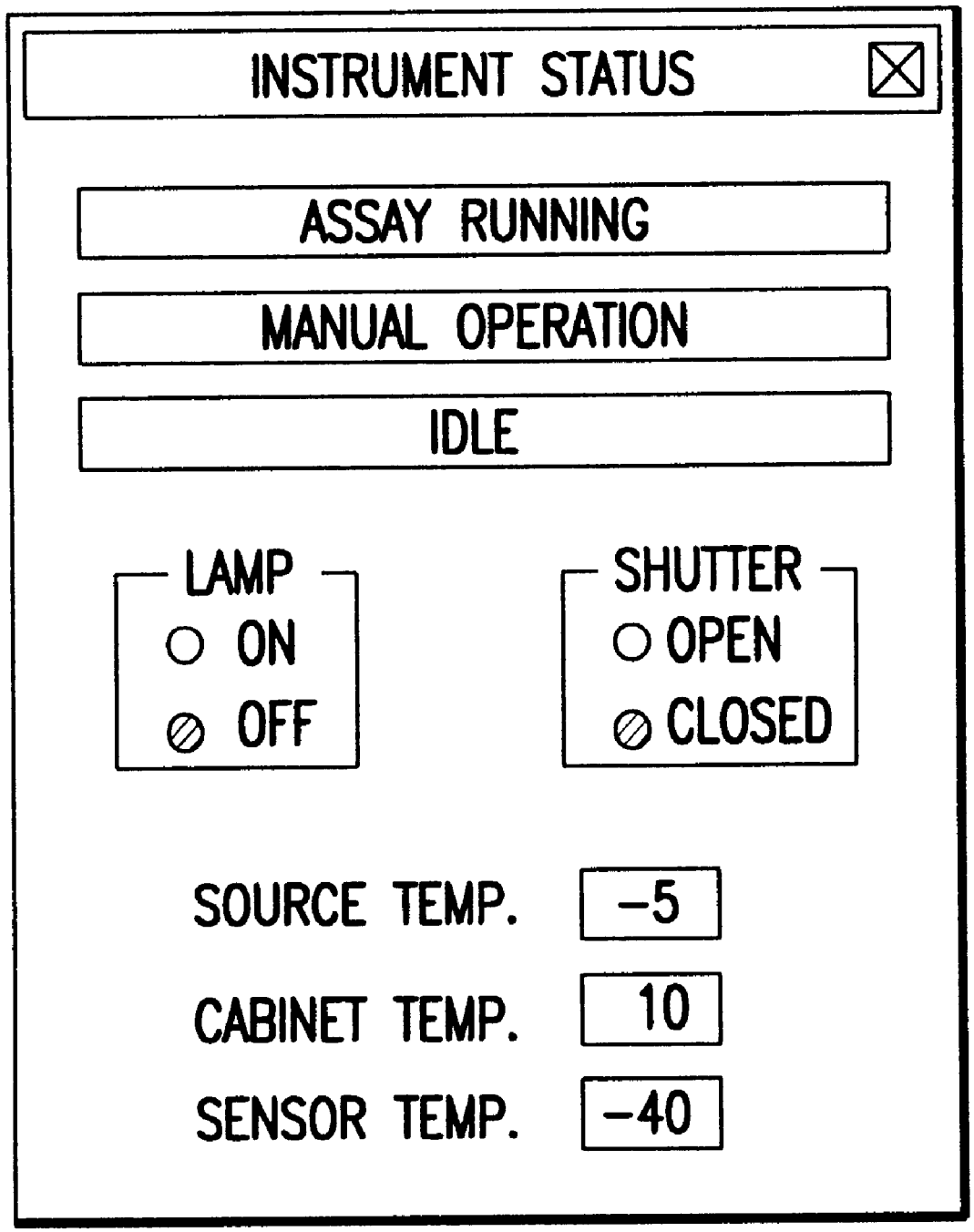
FIG. 9A is a diagram of the status feedback panel displayed on user interface monitor 403 which indicates to the operator the status of operation of the fluorimetry system.

The "run protocols" module 704 of the user operation system shown in FIG. 7 allows the operator to start and stop operation of the fluorimetry system and to monitor the operating status of the system. For example, FIG. 9A illustrates an example of a status/feedback panel showing the instrument status of the fluorimetry system, including the operating status, the lamp and shutter operating status, and various temperature readings.

Figure 9B:
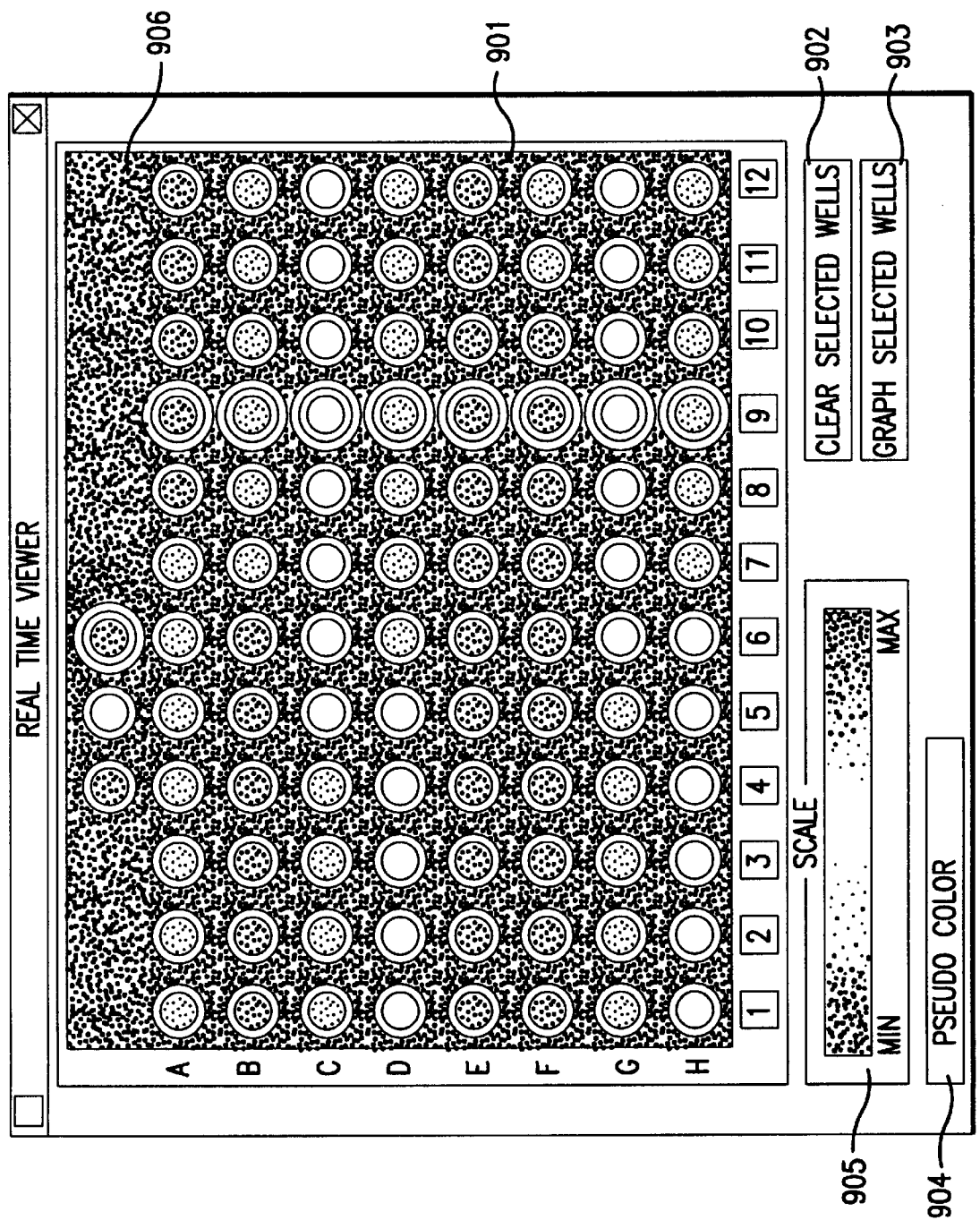
FIG. 9B is a diagram of the real-time viewer displayed on user interface monitor 403 which displays the test results as they are detected by the detector of the fluorimetry system.
Figure 9C:
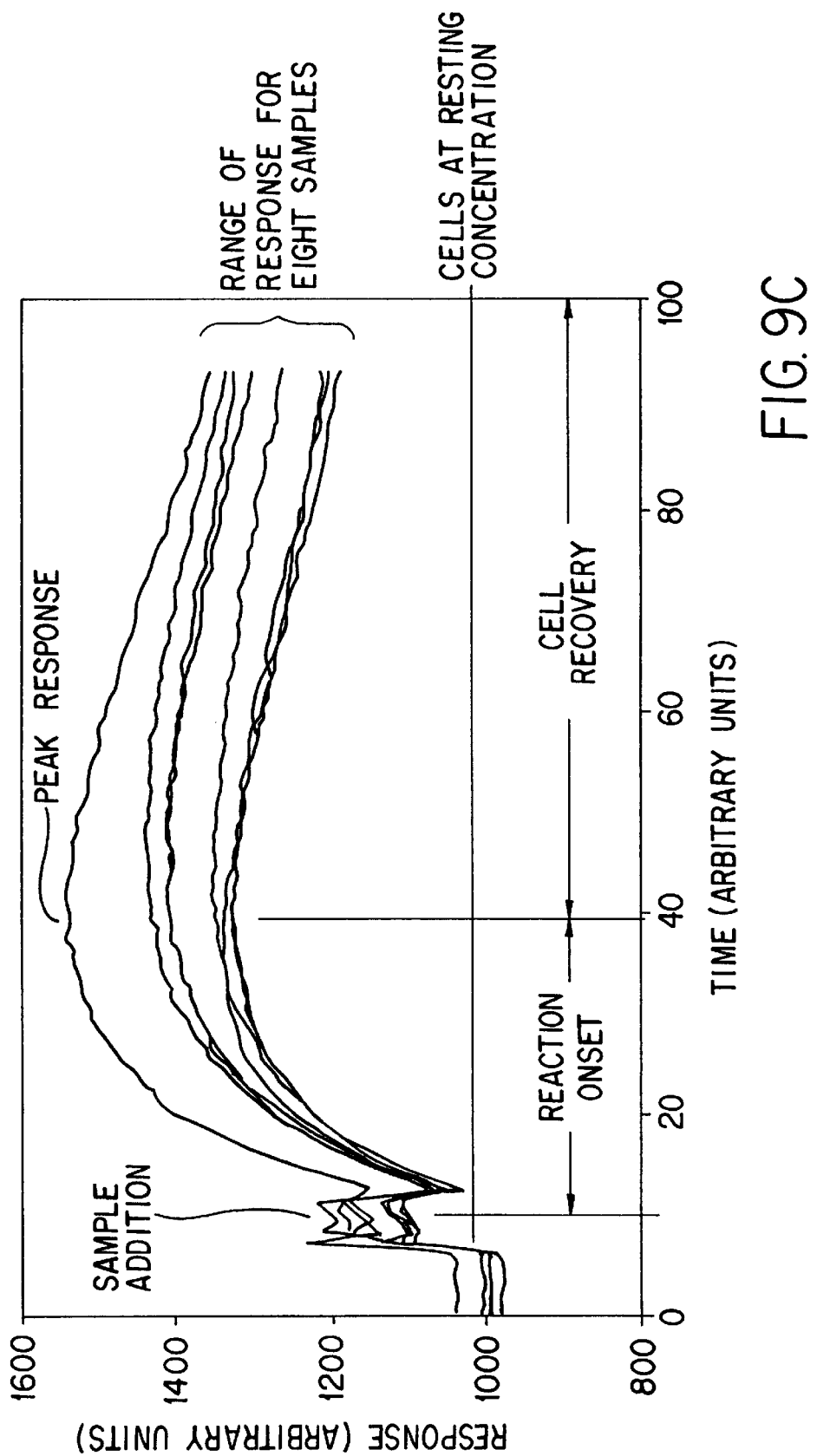
FIG. 9C provides an illustration of sample test results displayed in graph format on user interface monitor 403 including sample cell fluorescent response versus time curves for eight sample wells.

The "view and analyze data" module 705 of the user operation system shown in FIG. 7 allows an operator to view and analyze the data collected by the fluorimeter. The operator may access a single sample report generator 720 which automatically generates result reports for multiple samples. FIG. 9C illustrates an example of a result report in which a real-time viewer screen is displayed showing the status of the fluorescent readings from the wells being tested. The operator can also access a dose-response analysis module (721) which enables the operator to pick test compounds of interest and other distinguishing parameters which are then displayed in graphic form. In FIG. 9B, the fluorescent emissions from each well of the plate being tested are simultaneously displayed in window 901. The calibration regions 906 are provided, one black, one fluorescent, and one diffuse (from left to right), to enable comparison with the test reactions. A scale 905 is also provided to enable an evaluation of the fluorescence measurements as they are collected. Pseudo-color may also be provided by selecting function square 904, providing enhanced illustration of the fluorescence as it is collected or in pseudo real-time. Function squares 902 and 903 are also provided to respectively enable the operator to clear the display or graph the fluorescence readings, for example, as shown in FIG. 9C.

FIG. 9C illustrates a different type of display, an example of a graphic display of the fluorescence in eight wells versus time. This type of graphic information may be displayed in pseudo real-time for any selected number of wells as the assays are performed or after the assays have been completed. Other types of graphic displays such as fluorescence versus dosage may also be generated as desired by the operator. The operator may also access a data export tool module 722 from the "view and analyze data" module 705. The data export tool module enables the operator to select data sets through a database interface and to create ASCII or other types of data files to store and/or export the selected sets of data.

Figure 10:
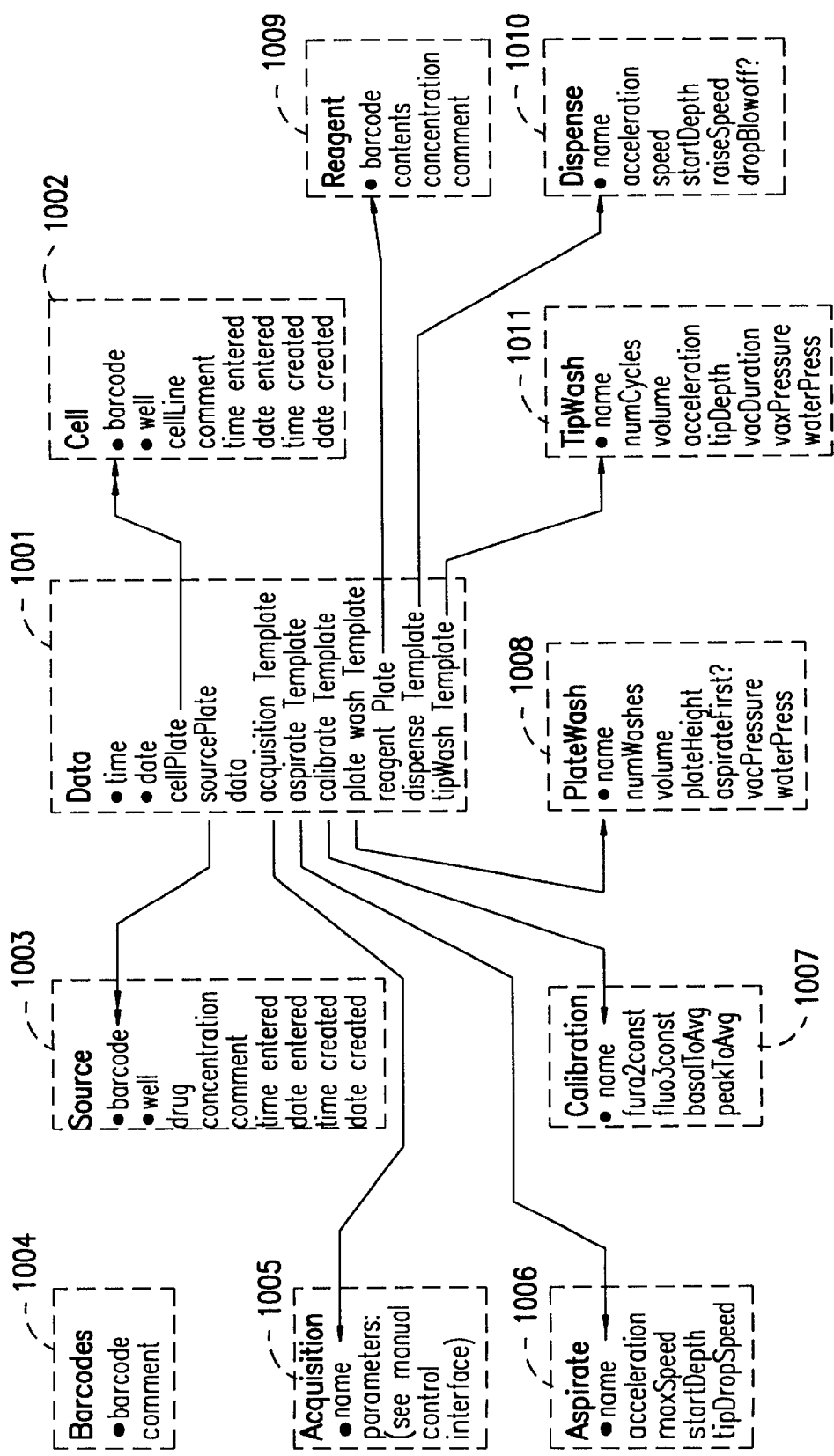
FIG. 10 provides a diagram of the database structure of the database stored in the hard disk of the user interface controller shown in FIG. 4.

With reference to FIG. 10, one possible database structure of the relational database stored on the hard disk 405 of user interface controller 402 is shown. The database includes a data table 1001 which acquires data from other tables as needed. The data table 1001 stores time and date fields, and accesses data stored in cell table 1002, source table 1003, barcodes table 1004, acquisition table 1005, aspirate table 1006, calibration table 1007, platewash table 1008, reagent table 1009, dispense table 1010, and tipwash table 1011. The data stored in cell table 1002 includes barcode data and well data including cell line data, comment data, time entered data, date entered data, time created data, and date created data. The data stored in source table 1003 includes barcode data and well data including drug data, concentration data, comment data, time entered data, date entered data, time created data, and date created data. Data stored in barcodes table 1004 includes barcode data including comment data. The data stored in acquisition table 1005 includes data entered into all fields of the acquisition template editor shown in FIG. 8C. Similarly, the data contained in aspirate table 1006 and dispense table 1010 includes all fields shown on the aspirate and dispense template editors in FIG. 8D. The data stored in calibration table 1007 includes all fields entered using the calibration template editor shown in FIG. 8B, and the platewash table 1008 and tipwash table 1011 contain fields corresponding to all data entered using the respective template editors shown in FIG. 8E.

Operation of the Fluorimetry System According to the Present Invention

With reference to FIG. 1, the operation of the fluorimetry system according to the present invention will now be described by outlining the procedures used in a typical assay. In accordance with the present invention, the system performs typical assays and other selected operations based on the definitions entered by the operator using the scheduler and, for example, the screens described with reference to FIGS. 8A–E. The robotic arm and pipette 102 will first prepare a plate 204 in which assays will be performed containing appropriate cells, with signal-generating elements (e.g., a fluorescent indicator) and any other required components. The bar code of the test source plate and the plate 204 is read by bar code reader 105 and provided to the system controller 110. The plate 204 is then placed over the fluorimeter port 103, and baseline data (used for calibration of the fluorimeter as described below) is collected using camera 203 and excitation source 205. A full resolution image is taken at this point to record the general quality and characteristics of the plate. The test source plate containing, e.g., a liquid solution is then placed under the 96-tip pipetting head at transfer station 112 and aspirated.

With reference to FIG. 6, the fluorimeter then begins to collect fluorescence data using excitation source 205 and camera 203, and the pipetting head 202 is programmed to dispense a compound to be tested from pipettor 201 at a predetermined time. During collection of fluorescence response data, some pseudo real-time response information may be displayed. When the collection of response information is complete, another full resolution image of the plate 204 is taken by the camera 203 of the fluorimeter 200. Next, any calibration operations are performed to determine $F_{max}$ (maximum fluorescence reading) and $F_{min}$ (minimum fluorescence reading) for the indicator, such as cell lysis and indicator quenching. Cell lysis is the process of adding detergent or another solution to break the membranes of the test cells in order to release all of the calcium or relevant ion within the cell. This enables the maximum reaction between the calcium ore relevant ion within the cells and the fluorescent indicator and thus yields the maximum possible fluorescence of the indicator ($F_{max}$). Indicator quenching is the process of adding a solution to displace calcium ions from the indicator molecules so that they are no longer fluorescent, thus the minimum fluorescence ($F_{min}$) of the indicator can be determined. The maximum and minimum fluorescence values are required in calculating the ion concentrations. Finally, all of the collected data is analyzed to produce a dose response curve or any other desired type of response display which is available to the operator. All of the data associated with the assay is recorded in a database for future reference and study.

With reference to FIGS. 1 and 6, one possible assay process in which twenty-five 96-well plates with pre-plated cells are automatically tested will now be described in greater detail. The assays are defined, for example, by an operator with the scheduler and the screens described with reference to FIGS. 8A–8E. Test liquid solution source plates, indicator source plates, lysis buffer source plates and quench solution source plates sufficient to perform complete assays for the twenty-five sample plates are supplied to the fluorimetry system. Once the fluorimetry system has been adequately supplied, the following procedure is repeated twenty-five times, once for each 96-well plate, without additional operator input. This procedure is not limited to 25 plates, and can be extended by increasing the plate storage capacity of the system.

First, the robot arm 102 prepares a 96-well plate 204 containing cells by washing the plate 204 three times in the plate washer 113. The robot arm 102 moves the 96-well plate 204 to the fluorimeter port 103. The upper housing 210 is lowered and a low- and high-resolution image is recorded. The robot arm 102 moves the 96-well plate 204 to the plate washer 113 where the buffer solution is aspirated. The robot arm 102 then moves the plate 204 to fluorimeter part 103. Indicator is then loaded into the plate 204 from an indicator source plate using the 96-tip pipetting tips 202. The plate 204 is then moved by robot arm 102 to incubator 107 incubated in incubator 107 for two hours, during which the pipetting tips 202 are washed in tip washer 108. Following the incubation of the plate 204, the plate 204 is again washed in plate washer 113. The plate 204 is now ready to be tested.

The 96-tip pipetting tips 202 are loaded with a liquid, e.g. a sample compound in solution, from the source plate. The cell plate 204 is positioned in the fluorimeter port 103 over the camera 203 and excitation source 205 of the fluorimeter 200 as shown in FIG. 6, and the camera 203 begins to read the fluorescence emitted from the plate 204 to obtain a series of fluorescence readings called "basal fluorescence" readings which indicate the fluorescence generated by the plate, cells, and indicator before the reagent is added. The basal fluorescence may be subtracted from the response fluorescence readings obtained during the reactions within the wells to provide an accurate reading of the fluorescence produced as a result of interaction of the added solution, e.g., sample reagent, and the cells.

Once basal fluorescence readings have been taken, the pipetting head 202 is lowered, sample reagent dispensed from pipettor 201 into each of the wells on the plate 204, and the pipetting head 202 is raised away from the plate 204. The camera 203 continues reading the response fluorescence of the wells during dispersion of the sample reagent and for a period of time thereafter.

Once the fluorescence reading is discontinued after the selected period of time has passed, the pipette tips 201 are washed in the tip washer 108, and lysis buffer is added to the plate 204 from the lysis buffer source plate using the 96-tip pipetting head 202. The plate 204 is incubated for five minutes in incubator 107, during which the pipette tips 201 are washed again in tip washer 108. The plate 204 is then read again by the camera 203 of the fluorimeter 200 for one second to obtain the maximum possible fluorescence of the reaction in the wells of the plate 204. Then, the quench solution is added to the plate 204 from the quench source plate using pipetting tips 202. The plate is again moved to the incubator 107 by robot arm 102 and incubated in incubator 107, this time for one minute, during which the pipetting tips 201 are again washed in tip washer 108. The plate 204 is returned to the fluorimeter port 103 by robot arm 102 and again read by the camera 203 of fluorimeter 200 for one second to obtain the minimum fluorescence reading for the wells on the plate 204. Once testing has been completed, the plate 204 is discarded, and the tip-holding plate 201 on the pipetting head 202 is automatically replaced.

The calibration of the data will now be described in further detail. A first fluorescence reading, labelled autofluorescence, is taken of the plate including pre-plated cells by the camera 203 of the fluorimeter 200. When the indicator has been added to the wells, incubated, and washed off of the plate 204, a second series of fluorescence readings, the basal fluorescence readings, is taken to indicate the fluorescence of the plate, cells, and indicator together prior to the addition of the test sample reagents. While the camera 203 of fluorimeter 200 continues to take fluorescence readings, the test sample reagents are added to the sample wells using the 96-tip pipetting head 202. A third series of fluorescence readings called response fluorescence data then is taken as the test samples and cells interact in the wells for a predetermined period of time. A lysis solution is added to permeabilize the cell membranes and release all of the indicator within the cell to create the maximum possible fluorescence of the assay. Finally, a quenching solution is added to displace the indicator molecules from the ions to determine the minimum fluorescence from the indicator. From this final quenched state of the assays, the minimum fluorescence reading of the assay can be taken for each well on plate 204. All of the data sets taken are combined with chemical constants in a mathematical formula which when applied to the response readings, yield calibrated response in units of ion concentration.

According to another possible assay method of the fluorimetry system of the present invention, a ratioing process is used in which the fluorescent indicator in the well is exposed to excitation light of two different wavelengths instead of one (as used in the above-described non-ratioed assays). For example, the excitation source delivers excitation radiation alternating between 350 nm and 385 nm. Filter wheel 212 is rotated back and forth to produce light of the two different wavelengths required for ratioed testing.

In ratioed testing, the fluorescence of each assay is monitored at both excitation wavelengths, and the fluorescence reading for one wavelength is divided by the fluorescence reading for the other wavelength to produce a test result independent of any external factors such as indicator concentration, changes in cell size and volume, indicator leakage, etc. As a result, test results obtained from ratioed tests are less subject to noise and drift errors that can occur during testing, for example, if the strength of the excitation source drifts during the test period. In ratioed testing, these factors are present for each fluorescence reading and are therefore eliminated when one fluorescence reading is divided by the other.

Ratioed testing provides for increased accuracy of signal measurement by ratioing the signals measured after excitation with light of one wavelength and excitation with light of a second different wavelength. The ratio of two emitted light measurements can be a more accurate determination of the actual emitted light than single absolute measurements because the ratio cancels the effects of instrument drift, transient changes in instrument sensitivity and changes in cell volume or fluorescent indicator concentration, each of which may be mistaken for a change in the attribute being measured.

Operation of the fluorimetry system according to the present invention is controlled, for example, by an operator using computer control tools such as those shown in FIGS. 8A–E. For example, an operator can use the data entry tool shown in FIG. 8A to enter information about the plate to be used. The bar code of the plate is entered in field 801, and the date and time of the testing are entered into fields 802 and 803 respectively. Command squares 804, 805, and 806 allow the operator to save the entered plate information, pull up a new entry screen for a new plate, or delete plate information already entered. The cell line is entered into field 807, and optional comments may be entered into field 808. The operator may select a specific well in order to enter the appropriate cell line in window 809, and a diagram of the plate is provided in window 810 which illustrates the arrangement and numbering of the wells on the plate. Following entry of plate information, the operator may store the information in the database stored in the hard disk 405 of user interface controller 402. The operator may then enter information for other plates, source plates, reagent plates, or other types of plates used during the operation of the fluorimetry system.

The operator may also use, for example, the calibration template editor shown in FIG. 8B to set calibration parameters for the fluorimeter 200. The operator enters the chemical constants into fields 811 and 812. The number of basal points to average is entered into field 813 using sliding bar 814. Similarly, the number of peak points to average is entered into field 815 using sliding bar 816. The parameters entered by the operator are stored in the database of the user interface controller 402.

As shown in FIG. 8C, the Acquisition Template Editor allows the user to create and modify templates which the system uses to collect data with the fluorimeter. The majority of the controls on this editor set camera parameters. The other controls are for the excitation source and for setting up pipette dispense operations during collections.

The box labeled 822 in FIG. 8C contains the two controls which are used to set up a pipette dispense during the collection. The button determines whether a dispense should occur at all during the collection. If the button is checked, then the fluorimeter will initiate a dispense after the frame number entered in the text field.

Box 817 contains the source parameter controls. The top-most button determines whether the shutter will be open or closed. The filter control box 818 allows the user to set the filter numbers to be used. If the numbers are different in the two fields, the filter wheel will switch filters each frame between the two selected. The pop-up list below these fields provides a reference list so that the user can see what the filter numbers correspond to. The iris slider 819 sets the position of the iris between zero for closed and 100 for open. The last control is a button labeled "Do it Now." If this button is pushed, the source controls immediately affect the source. This allows the user to manually control the source for testing and measurement.

The CCD camera 203 used in the fluorimeter system is very flexible (as described above with reference to FIGS. 3A and 3B), and therefore requires sophisticated controls. The controls can be divided into two groups, those that control what part of the CCD is read, and those that determine the readout timing. The primary readout region control is the image displaying view 831. The user loads an image into this view by pressing the "Grab Full Res." button 825. If the "Readout Regions" button in box 829 is checked, this view will overlay the regions of the chip to be read. The number of regions shown is determined by the rows and columns text fields in box 823. The position and size of these regions in view 831 may be directly manipulated, for example, by using a mouse. The binning text field in box 823 sets the number of rows and columns to be summed on the chip before readout occurs. Higher binning values improve speed and lower noise at the expense of spatial resolution.

The user tells the system to sum pixels in real time by checking the "Sum Pixels" button in box 823. This will cause the real time controller to sum the pixels in the ellipses inscribed in the rectangular readout regions after they are read out. These ellipses are displayed if the "Integration Circles" button is checked in box 829. The "sum pixels" mode corresponds to that depicted in FIG. 3B.

The readout timing controls set the speed of reading individual pixels as well as frame timing. The readout speed is controlled by the "fast" button in the A/D (analog to digital) converter box 821. If this button is checked, the A/D converter runs at 100 kHz, otherwise it runs at 40 kHz. The antibloom slider box in 821 determines the level of antibloom compensation used. The amount of time the CCD is exposed to light is controlled by the "Integration Time" text field 824.

The rate at which frames are collected and the total number of frames collected is controlled by view 827. This view is a graph with the frame rate on the vertical axis and the duration of the collection on the horizontal axis. A cross hair shows the currently selected frame rate and collection time. The user may move this cross hair, for example, using a mouse, to choose the combination desired. The number of frames to be collected is the product of the frame rate and the collection time, and is displayed next to the cross hair. The arrows at the end of each axis expand or contract the scale used by the associated axis. The scale adjustment allows a broad range of possible selections while still providing fine control. The "Center Cursor" button adjusts the scales so that the cursor is centered in the view. This is provided because it is possible to lose the cursor while adjusting the scales.

The view 827 has a red region (gray in FIG. 8C) and a green region (white in FIG. 8C). The red region indicates that combinations in this part of the graph are impossible for the camera 203 to achieve. For example, the amount of the chip to be read, the A/D conversion speed and the integration time all limit the maximum frame rate. Similarly, if pixels are not summed in real time, the camera controller will eventually run out of memory, limiting the maximum number of frames. The software that controls this view will not allow the user to place the cross hair in the red region. The software adjusts the red region boundary as other related settings are adjusted.

Before a collection is begun, the user may specify two set-up actions. The first is that the chip be read and the data discarded to remove any thermal electrons that may have been generated since the last collection. The number of cleanup frames is set by the text field in box 820. The second action is that a full resolution frame be grabbed so that the quality of the plate may be recorded. This is selected by checking the "Collect Initial Full Res. Frame" button in box 820.

There are some display controls that do not affect the template which are provided for the convenience of the user. If the "Do Acquire" button 826 is pressed, the entire collection described by the current template is executed. If this template specifies multiple frames, the "Frame Number" text field in box 829 is used to specify the frame to be displayed. The color map controls in box 830 allows the user to set the scaling parameters and false color map to be used in view 831. The "Summed Value" controls in box 828 allow the user to specify up to three regions in the display to be summed. The resulting sums are displayed in the three text fields.

The name field 832 shows the name of the template being edited. Another panel (not shown) presents a list of all the templates that have been created. The user may select the template to be edited from this list. The user may also make new templates by copying old ones with the push of a button. When a new selection is made or a new template created, the parameters and name in the template editor are changed to match.

Pipette operation template editors, for example, those shown in FIG. 8D, may be used to set parameters for the pipette operation of the fluorimetry system. In the template editors shown in FIG. 8D, one template sets parameters for pipette aspiration and one for pipette dispensing. The acceleration of the pipette for each operation is entered into field 840 using sliding bar 841. Similarly, the maximum speed of the pipette for each operation is entered into field 842 using sliding bar 843, tip start depth is entered into field 844 using sliding bar 845, and tip drop speed for each operation is entered into field 846 using sliding bar 847. A drop blow off option following the dispense operation of the pipetting head 202 may be selected by selecting box 848. The time to complete pipette operation is also displayed on the screen at 849. The parameters entered by the operator are then stored in the database of user interface controller 402.

The operator may also control the washing operation of the fluorimetry system, for example, using the washing operation template editors shown in FIG. 8E. To set plate washing parameters, the operator selects whether aspiration or dispensing will occur first using selection boxes 850. The number of washes is entered into field 851 using sliding bar 852, the dispense time is entered into field 853 using sliding bar 854, and the plate height is entered into field 855 using sliding bar 856. Manually-set parameters such as vacuum pressure and water pressure may be entered into fields 857 and 858 respectively. The time to complete washing is displayed at 859. Similarly, to select tip washing parameters, the number of pipette cycles is entered into field 860 using sliding bar 861, the pipette volume is entered into field 862 using sliding bar 863, the pipette acceleration is entered into field 864 using sliding bar 865, the tip depth is entered into field 866 using sliding bar 867, and the vacuum duration is entered into field 868 using sliding bar 869. Manually set parameters such as vacuum pressure and water pressure are entered into fields 870 and 871 respectively, and the time to complete washing is displayed at 872. The parameters entered by the operator are stored in the database of user interface controller 402.

One application of the system according to the present invention is drug screening, wherein compounds in solution are tested to identify compositions having the ability to activate, potentiate, or inhibit ion channels and/or receptors of a cell, such that the ion channel or receptor, when activated, directly or indirectly contributes to a detectable change in the level of a predetermined ion in the cell. The cell contains an ion-sensitive indicator which is sensitive to the predetermined ion.

Drug screening assays that may be performed by the system according to the present invention will now be described in greater detail. In accordance with various assays performed by the system of the present invention, cells are employed which have ion channels and/or receptors, the activation of which results in a change in the level of a cation or anion in the cell. The cells employed are loaded with a fluorescent indicator or indicator which is sufficiently sensitive to the cation or anion. A sufficiently sensitive indicator is one which is capable of producing distinguishable levels of the fluorescence intensity in the presence of, and over a range of physiological concentrations of, a particular ion (cation or anion). Preferably, the fluorescent indicator should be able to produce detectably different intensities of fluorescence in response to relatively small changes in ion concentration. The relative intensities of fluorescence when the receptors or ion channels have not been activated, as compared to when the receptors or ion channels have been activated, should differ by at least 50% or more, preferably 100% to 200%.

One type of assay that may be performed by the system according to the present invention, which is used to determine ion channel or receptor activity and compounds that affect this activity, is a "direct" assay. As used herein, direct assays describe assays employing cells loaded with a fluorescent indicator capable of binding a specific ion. In such assays, the cells have ion channels or receptors that are permeable to said ions when activated. Such direct assays may be performed, for example, to assay cells loaded with a calcium-sensitive fluorescent indicator and having receptors and/or ion channels that are permeable to calcium (e.g., calcium channels or N-methyl-D-aspartate (NMDA) receptors); cells loaded with a chloride-sensitive fluorescent indicator and having receptors permeable to chloride ions (e.g., GABA receptors); and cells loaded with sodium or potassium-sensitive indicators and having receptors which are permeable to sodium and/or potassium ions (e.g., kainate/AMPA receptors, nicotinic acetylcholine receptors, sodium channels or potassium channels).

A second type of assay that may be performed by the system according to the present invention is an "indirect" assay. Indirect assays utilize a characteristic depolarization caused by the passage of ions through receptors which are ligand-gated ion channels. Such indirect assays employ cells having voltage-dependent calcium channels and the ligand-gated ion channels of interest. Activation of the ligand-gated ion channel allows ions to flow through the channel, depolarizing the cell membrane which in turn activates voltage-dependent calcium channels and results in the flow of calcium ions into the cell. The cells are loaded with a calcium-sensitive indicator. For example, activation of the nicotinic acetylcholine receptors by nicotine results in an influx of sodium ions, depolarizing the cell membrane and, consequently, activating voltage-dependent calcium channels. The degree of activation of the nicotinic acetylcholine receptors is measured indirectly by the flow of calcium ions through activated calcium channels. Among the known ligand-gated ion channels that can be assayed in this manner are certain kainate/AMPA-type excitatory amino acids (EAA) receptors.

Any cell expressing a receptor protein which is capable, upon activation, of directly increasing the intracellular concentration of an ion, such as by opening gated calcium channels, or indirectly affecting the concentration of an intracellular ion as by causing initiation of a reaction which utilizes $Ca^{2+}$ as a second messenger (e.g., G-protein-coupled receptors), may be used in the assay. Cells expressing such receptors or ion channels and cells which may be transfected with a suitable vector encoding one or more such cell surface proteins are known to those of skill in the art or may be identified by those of skill in the art. Further, many cells are known that may be genetically engineered to express a heterologous cell surface protein. A list of some possible cells is provided at page 36 of the disclosure of International Application No. PCT/US92/11090, filed Dec. 18, 1992, and published on Jul. 8, 1993, which is hereby incorporated by reference into the present disclosure. This international application also provides a list of some possible exemplary cell surface proteins at pages 36–38, a list of some possible ion channels at page 38, and a table of some possible ion-sensitive indicators at page 41. This international application further provides additional descriptions of types of assays that may be performed using the system according to the present invention.

Activation of the cellular receptors in the assays described above may result in a transient increase in the level of an intracellular ion. The initial increase in concentration may be detected as an increase in fluorescence within as little as one to two seconds after the addition of the reagent which activates the receptors and/or ion channels and is usually short-lived. Fluorescence levels in the cell typically increase to a peak value and then typically decline as excess ions are removed by normal cellular mechanisms. Typically, receptor or ion channel activation causes fluorescence levels to peak within about 5 to 45 seconds followed by reduction in fluorescence for about 2 to 20 minutes until intracellular calcium levels approach pre-activation levels. The speed at which the fluorescence can be analyzed is very important due to the kinetics of the response reaction contributed by an increase in ions in the cell followed by a subsequent decrease in the level of ions as they are removed from the cell.

The system according to the present invention can also be modified to perform other types of signal-based assays of a plurality of compounds based on luminescent reactions, signal absorbance, radioactivity, or any emissions emitted from the plurality of wells on a plate. For example, in the context of luminescent testing, the excitation source can be omitted from the system, such that the system would consist of an automatic and simultaneously controlled robotic fluid handling system, detection system (without the excitation source), and computer controlled data acquisition and analysis system.

While the present invention has been particularly described with reference to the preferred embodiments, it should be readily apparent to those of ordinary skill in the art that changes and modifications in form and details may be made without departing from the spirit and scope of the invention. It is intended that the appended claims include such changes and modifications.

We claim:

1. A method for simultaneously performing a plurality of fluorescence assays using a multi-well plate containing a plurality of wells distributed throughout at least a portion of said multi-well plate, said method comprising the steps of:

distributing a predetermined amount of a liquid to a number of said plurality of wells;

projecting excitation radiation uniformly onto the portion of said multi-well plate throughout which the plurality of wells are distributed, thereby simultaneously and uniformly illuminating both said plurality of wells and the portion that is disposed between each of said plurality of wells;

receiving an image of fluorescence emitted from said plurality of wells simultaneously over a predetermined period of time; and processing fluorescence data from the image.

2. The method according to claim 1, wherein said plurality of wells are exposed to a plurality of excitation wavelengths and the fluorescence emitted by said plurality of wells is determined upon excitation at each of said plurality of wavelengths.

3. The method according to claim 1, further including the step of creating a time series of pixel images of each of said plurality of wells to determine the fluorescence of each of said plurality of wells over said predetermined period of time.

4. The method of claim 1, further including the step of a computerized control means simultaneously controlling and coordinating said steps of distributing, projecting, receiving, and processing.

5. A method for simultaneously performing a plurality of signal-based assays, each of said plurality of assays performed in one of a plurality of wells on a multi-well plate, said method comprising the steps of:

distributing a predetermined amount of a liquid to a number of said plurality of wells;

receiving an image of emissions emitted from said plurality of wells simultaneously over a predetermined period of time, the image comprising an entire view of each of the plurality of wells; and processing emissions data from the received image.

6. The method according to claim 5, further including the step of creating a time series of pixel images of each of said plurality of wells to determine an amount of optical emissions of said reaction in each of said plurality of wells over said predetermined period of time.

7. The method according to claim 6, wherein said optical emissions are fluorescent emissions.

8. The method according to claim 6, wherein said optical emissions are luminescent emissions.

9. The method according to claim 5, wherein said emmissions are radioactive emissions.

10. The method of claim 5, further including the step of a computerized control means simultaneously controlling and coordinating said steps of distributing, receiving, and processing.

11. A method for simultaneously performing a plurality of drug screening assays, each of said plurality of assays performed in one of a plurality of wells on a multi-well plate, said method comprising the steps of:

providing a number of said plurality of wells with viable cells having functional ion channels and/or receptors which, when activated, directly or indirectly cause a detectable change in a concentration of a predetermined ion in said viable cells, wherein said viable cells contain an amount of an ion-sensitive indicator sufficient to detect a change, if any, in said concentration of said predetermined ion;

distributing a predetermined amount of an ion channel-activating or receptor-activating compound being tested for its ability to activate said ion channel or receptor to a number of said plurality of wells;

receiving an image of optical emissions emitted by said ion-sensitive indicator in said plurality of wells simultaneously over a predetermined period of time, the image comprising an entire view of each of the plurality of wells;

creating a time series of pixel images of said plurality of wells to determine an amount of said optical emissions of said ion-sensitive indicator in each of said plurality of wells over said predetermined period of time; and processing optical emissions data from the image.

12. The method according to claim 11, wherein said optical emissions are fluorescent emissions and said ion-sensitive indicator is an ion-sensitive fluorescent indicator.

13. The method of claim 11, further including the step of a computerized control means simultaneously controlling and coordinating said steps of distributing, receiving, and processing.

14. A method for simultaneously performing a plurality of drug screening assays, each of said plurality of assays performed in one of a plurality of wells on a multi-well plate, said method comprising the steps of:

providing a number of said plurality of wells with viable cells having functional ion channels and/or receptors which, when activated, are capable of directly or indirectly causing a detectable change in a concentration of a predetermined ion in said viable cells, wherein said viable cells contain an amount of an ion-sensitive indicator sufficient to detect a change, if any, in said concentration of said predetermined ion;

first distributing a first predetermined amount of a known ion channel-activating or receptor-activating compound to a number of said plurality of wells;

second distributing a second predetermined amount of an ion channel-inhibiting or receptor-inhibiting compound, said ion channel-inhibiting or receptor-inhibiting compound added to said number of said plurality of wells prior to or simultaneously with said ion channel-activating or receptor-activating compound;

receiving an image of optical emissions emitted by said ion-sensitive indicator in said plurality of wells over a predetermined period of time, the image comprising an entire view of each of said plurality of wells;

creating a time series of pixel images of said plurality of wells to determine an amount of said optical emissions of said ion-sensitive indicator in each of said plurality of wells over said predetermined period of time; and processing optical emissions data from the image.

15. The method of claim 14, further including the step of a computerized control means simultaneously controlling and coordinating said steps of first distributing, second distributing, receiving, and processing.

16. A method for simultaneously performing a plurality of fluorescence assays using a multi-well plate containing a plurality of wells distributed throughout at least a portion of said multi-well plate, the method comprising the steps of:

projecting excitation radiation uniformly onto the portion of the plate throughout which the plurality of wells are distributed, thereby simultaneously and uniformly illuminating both said plurality of wells and the portion that is disposed between each of said plurality of wells; and receiving an image of fluorescence emitted from the plurality of wells simultaneously and continuously over a predetermined period of time.

17. The method of claim 16, where the excitation radiation is projected as a collimated beam.

18. A method for scheduling and performing a plurality of fluorescence assays using a plurality of plates each including a plurality of wells, the method comprising the steps of:

storing data representing at least first and second tracks and at least one critical point at which the first and second tracks are tied together in time, each of the first and second tracks defining a set of assay operations in time, at least a portion of the set of assay operations of the first track to be performed simultaneously with the second track; and performing at least a portion of the sets of assay operations on at least one of the plates such that a portion of the set of assay operations of the second track defined prior to the at least one critical point is finished before beginning a portion of the set of assay operations of the first track defined after the at least one critical point.

19. The method of claim 18 further including the step of determining a total time to run all of the sets of assay operations of the first and second tracks.

20. The method of claim 19 further including the step of rearranging at least a portion of the sets of assay operations of at least one of the first and second tracks according to the total time to run all of the sets of assay operations of the first and second tracks.

21. The method of claim 18 further including the step of defining the first and second tracks using a graphic user interface.

22. A method for simultaneously performing a plurality of fluorescence assays using a plate containing a plurality of wells, the method comprising the steps of:

detecting fluorescence emitted from each of the plurality of wells; and displaying in real or pseudo real time a graphical representation of the fluorescence emitted from each of the plurality of wells, the graphical representation indicating an arrangement in the plate of the plurality of wells.

23. The method of claim 22 wherein the step of displaying includes displaying the graphical representation including a plurality of regions each having a particular brightness depending upon the fluorescence of at least one of the plurality of wells.

24. The method of claim 22 wherein the step of displaying includes displaying the graphical representation including a plurality of regions each having a particular color or a particular pseudo-color depending upon the fluorescence of at least one of the plurality of wells.

25. A method for simultaneously performing a plurality of fluorescence assays using a plate including a plurality of wells distributed throughout at least a portion of the plate, the method comprising the steps of:

alternately projecting a first excitation radiation having a first wavelength and a second excitation radiation having a second wavelength uniformly onto the portion of the plate throughout which the plurality of wells are distributed, thereby simultaneously and uniformly illuminating both the plurality of wells and the portion that is disposed between each of the plurality of wells;

detecting a first fluorescence emitted from each of the plurality of wells in response to the first excitation radiation and a second fluorescence emitted from each of the plurality of wells in response to the second excitation radiation to generate data representing an amount of the first and second fluorescence for each of the plurality of wells; and dividing the amount of the first fluorescence of at least one of the wells by the amount of the second fluorescence of the at least one of the wells to generate a test result.

* * * * *